United States Patent
Chen et al.

(10) Patent No.: US 9,778,391 B2
(45) Date of Patent: Oct. 3, 2017

(54) SYSTEMS AND METHODS FOR MULTI-VIEW IMAGING AND TOMOGRAPHY

(71) Applicant: Varex Imaging Corporation, Salt Lake City, UT (US)

(72) Inventors: Gongyin Chen, Henderson, NV (US); Kevin Holt, Chicago, IL (US); Robert E. Drubka, Scottsdale, AZ (US); John Stammetti, Las Vegas, NV (US); Michael Z. Duncan, Elgin, IL (US); Timothy R. Fox, Chicago, IL (US); David Nisius, Des Plaines, IL (US); Martin Hu, Deerfield, IL (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 220 days.

(21) Appl. No.: 14/218,699

(22) Filed: Mar. 18, 2014

(65) Prior Publication Data
US 2014/0294147 A1 Oct. 2, 2014

Related U.S. Application Data

(60) Provisional application No. 61/798,372, filed on Mar. 15, 2013.

(51) Int. Cl.
*G01V 5/00* (2006.01)
*G01N 23/04* (2006.01)
(Continued)

(52) U.S. Cl.
CPC .......... *G01V 5/0016* (2013.01); *G01N 23/04* (2013.01); *G01N 23/046* (2013.01); *G01V 5/005* (2013.01);
(Continued)

(58) Field of Classification Search
CPC .... G01V 5/0016; G01V 5/0041; G01V 5/005; G01V 5/0008; G01V 5/0025;
(Continued)

(56) References Cited

U.S. PATENT DOCUMENTS 5,504,791 A * 4/1996 Hell ...................... A61B 6/032
378/10
5,654,995 A * 8/1997 Flohr ................... A61B 6/4028
378/10

(Continued)

FOREIGN PATENT DOCUMENTS

JP 2004-174253 6/2004
JP 2004-174261 6/2004
(Continued)

OTHER PUBLICATIONS

Fessler, Jeffrey A., "Iterative image reconstruction for CT", EECS Dept., BME Dept., Dept. of Radiology University of Michigan, http://www.eecs.umich.edu/~fessler, AAPM Image Educational Course—Image Reconstruction 11, Aug. 2, 2011.

(Continued)

*Primary Examiner* — Allen C. Ho
(74) *Attorney, Agent, or Firm* — Cozen O'Connor; Brandon N. Sklar

(57) ABSTRACT

Radiation scanning systems providing multiple views of an object in different planes and a reconstruction algorithm for reconstructing quasi-three-dimensional images from a limited number of views. A system may include bend magnets to direct accelerated charged particles to multiple targets in different viewing locations. Another system collimates radiation generated by a plurality of radiation sources into multiple beams for scanning an object at multiple angles. The object may be a cargo container, for example. The reconstruction algorithm uses an optimization algorithm and (Continued)

imaging and feasibility models to reconstruct quasi-three-dimensional images from the limited number of views.

20 Claims, 12 Drawing Sheets

(51) Int. Cl.
  *H05H 7/22* (2006.01)
  *H05H 9/00* (2006.01)
(52) U.S. Cl.
  CPC .......... *G01V 5/0008* (2013.01); *G01V 5/0025* (2013.01); *G01V 5/0041* (2013.01); *G01V 5/0066* (2013.01); *H05H 7/22* (2013.01); *H05H 9/00* (2013.01)
(58) Field of Classification Search
  CPC .. G01V 5/0066; G01B 5/0025; G01B 5/0066; G01N 23/046; H05H 7/22; H05H 9/00
  USPC .................. 378/10, 12, 57, 86–90, 98.6, 119
  See application file for complete search history.

(56) References Cited

U.S. PATENT DOCUMENTS

| | | | | |
|---|---|---|---|---|
| 5,745,546 A * | 4/1998 | Hell | .................. | H01J 35/08 378/10 |
| 5,841,046 A | 11/1998 | Rhodes et al. | | |
| 5,841,831 A * | 11/1998 | Hell | .................. | A61B 6/4028 378/12 |
| 5,940,468 A * | 8/1999 | Huang | .................. | G01N 23/04 378/57 |
| 6,035,015 A * | 3/2000 | Ruth | .................. | G03F 7/70025 378/119 |
| 6,151,381 A * | 11/2000 | Grodzins | .................. | G01N 23/04 378/57 |
| 6,160,869 A * | 12/2000 | Zapalac | .................. | H01J 35/30 378/10 |
| 6,327,339 B1 * | 12/2001 | Chung | .................. | G21K 5/04 250/505.1 |
| 6,366,641 B1 * | 4/2002 | Whitham | .................. | H05H 9/04 250/492.3 |
| 6,369,585 B2 * | 4/2002 | Yao | .................. | G01R 23/04 324/633 |
| 6,407,505 B1 * | 6/2002 | Bertsche | .................. | H05H 9/04 315/5.41 |
| 6,421,420 B1 * | 7/2002 | Grodzins | .................. | G01N 23/20 378/113 |
| 6,493,424 B2 * | 12/2002 | Whitham | .................. | H05H 9/04 378/137 |
| 6,628,745 B1 * | 9/2003 | Annis | .................. | A61B 6/032 378/10 |
| 6,850,592 B2 * | 2/2005 | Schramm | .................. | G01N 23/223 162/57 |
| 6,937,692 B2 * | 8/2005 | Johnson | .................. | G01V 5/0016 378/55 |
| 7,020,241 B2 * | 3/2006 | Beneke | .................. | G01V 5/0016 378/54 |
| 7,060,981 B2 * | 6/2006 | Retterath | .................. | A22B 5/007 250/359.1 |
| 7,082,182 B2 * | 7/2006 | Zhou | .................. | A61B 6/032 378/10 |
| 7,099,433 B2 * | 8/2006 | Sommer | .................. | G01N 23/06 209/589 |
| 7,103,137 B2 * | 9/2006 | Seppi | .................. | G01N 23/04 378/57 |
| 7,203,269 B2 * | 4/2007 | Huber | .................. | H01J 35/06 378/10 |
| 7,208,889 B2 * | 4/2007 | Zavadtsev | .................. | G21K 5/04 250/396 R |
| 7,208,890 B2 * | 4/2007 | Zavadtsev | .................. | H05H 7/00 315/5.41 |
| 7,215,737 B2 * | 5/2007 | Li | .................. | G01V 5/0016 378/57 |
| 7,233,644 B1 * | 6/2007 | Bendahan | .................. | G01N 23/046 378/57 |
| 7,280,631 B2 * | 10/2007 | De Man | .................. | A61B 6/032 378/10 |
| 7,295,651 B2 * | 11/2007 | Delgado | .................. | G01N 23/046 378/10 |
| 7,319,737 B2 * | 1/2008 | Singh | .................. | G01N 23/046 378/57 |
| 7,333,587 B2 * | 2/2008 | De Man | .................. | A61B 6/032 378/16 |
| 7,356,116 B2 * | 4/2008 | Anwar | .................. | G01V 5/0016 378/57 |
| 7,356,118 B2 * | 4/2008 | Might | .................. | G01N 23/04 378/5 |
| 7,379,530 B2 * | 5/2008 | Hoff | .................. | G01V 5/0016 378/108 |
| 7,388,940 B1 * | 6/2008 | De Man | .................. | A61B 6/032 378/4 |
| 7,400,701 B1 * | 7/2008 | Cason | .................. | G01V 5/0025 378/57 |
| 7,428,292 B2 * | 9/2008 | De Man | .................. | A61B 6/032 378/4 |
| 7,453,987 B1 * | 11/2008 | Richardson | .................. | G01V 5/0041 378/57 |
| 7,505,562 B2 * | 3/2009 | Dinca | .................. | G01N 23/201 378/57 |
| 7,526,064 B2 * | 4/2009 | Akery | .................. | G01N 23/04 378/198 |
| 7,564,943 B2 * | 7/2009 | Sommer, Jr. | .................. | G01N 23/06 250/390.04 |
| 7,577,236 B2 * | 8/2009 | Nose | .................. | A61B 6/00 378/116 |
| 7,580,505 B2 * | 8/2009 | Kang | .................. | A61B 6/4241 378/54 |
| 7,606,348 B2 * | 10/2009 | Foland | .................. | G01N 23/046 378/4 |
| 7,606,349 B2 * | 10/2009 | Oreper | .................. | G01V 5/005 378/137 |
| 7,616,731 B2 * | 11/2009 | Pack | .................. | G01N 23/046 378/10 |
| 7,627,081 B2 * | 12/2009 | Bontus | .................. | A61B 6/032 378/4 |
| 7,634,045 B2 * | 12/2009 | Popescu | .................. | A61B 6/032 378/10 |
| 7,639,774 B2 * | 12/2009 | De Man | .................. | A61B 6/032 378/124 |
| 7,646,851 B2 * | 1/2010 | Liu | .................. | G01N 23/087 378/119 |
| 7,684,538 B2 * | 3/2010 | Morton | .................. | A61B 6/032 378/10 |
| 7,688,937 B2 * | 3/2010 | Schomberg | .................. | A61B 6/032 378/10 |
| 7,702,075 B2 * | 4/2010 | Wang | .................. | G01N 23/087 378/57 |
| 7,706,499 B2 * | 4/2010 | Pack | .................. | A61B 6/027 378/10 |
| 7,724,876 B2 * | 5/2010 | Nose | .................. | G21K 5/00 378/119 |
| 7,813,478 B2 * | 10/2010 | Nisius | .................. | G01N 23/04 378/115 |
| 7,831,012 B2 * | 11/2010 | Foland | .................. | G01N 23/04 378/57 |
| 7,835,486 B2 * | 11/2010 | Basu | .................. | G01T 1/2985 378/10 |
| 7,835,499 B2 * | 11/2010 | Yu | .................. | H01J 25/02 378/119 |
| 7,839,967 B2 * | 11/2010 | Grass | .................. | A61B 6/032 378/10 |
| 7,864,917 B2 * | 1/2011 | Ribbing | .................. | A61B 6/032 378/10 |
| 7,872,241 B2 * | 1/2011 | Rand | .................. | H01J 35/08 250/396 ML |
| 7,922,390 B2 | 4/2011 | Holt et al. | | |

(56) References Cited

U.S. PATENT DOCUMENTS

| | | | | |
|---|---|---|---|---|
| 7,991,117 B2* | 8/2011 | Chen | ............... | G01V 5/0016 378/108 |
| 8,000,448 B2* | 8/2011 | Nose | ............... | H05G 2/00 378/119 |
| 8,137,976 B2 | 3/2012 | Bjorkholm | | |
| 8,138,678 B2* | 3/2012 | Ishida | ............... | G21K 1/087 313/360.1 |
| 8,183,801 B2* | 5/2012 | Chen | ............... | H05H 7/02 315/500 |
| 8,184,769 B2* | 5/2012 | Fox | ............... | A61B 6/4035 378/53 |
| 8,198,587 B2* | 6/2012 | Whittum | ............... | G01V 5/0041 250/306 |
| 8,203,289 B2* | 6/2012 | Ho | ............... | H05H 9/04 315/505 |
| 8,222,598 B2* | 7/2012 | Statham | ............... | G01N 23/2252 250/305 |
| 8,223,918 B2* | 7/2012 | Johnson | ............... | G01V 5/0016 378/57 |
| 8,232,748 B2* | 7/2012 | Treas | ............... | H05H 7/02 250/390.1 |
| 8,233,682 B2* | 7/2012 | Fessler | ............... | A61B 6/032 378/49 |
| 8,284,898 B2* | 10/2012 | Ho | ............... | H05H 9/04 315/505 |
| 8,300,763 B2* | 10/2012 | Shedlock | ............... | G01N 23/046 378/57 |
| 8,311,187 B2* | 11/2012 | Treas | ............... | H05H 7/02 315/505 |
| 8,422,826 B2* | 4/2013 | Holt | ............... | G06T 5/50 345/634 |
| 8,457,274 B2* | 6/2013 | Arodzero | ............... | G01V 5/0041 378/53 |
| 8,508,545 B2* | 8/2013 | Holt | ............... | G06T 11/001 345/581 |
| 8,509,380 B2* | 8/2013 | Pelc | ............... | A61B 6/032 378/9 |
| 8,551,785 B2 | 10/2013 | Bjorkholm | | |
| 8,582,720 B2* | 11/2013 | Morton | ............... | G01V 5/0008 378/57 |
| 8,588,494 B2* | 11/2013 | De Man | ............... | G06T 11/008 378/18 |
| 8,644,549 B2* | 2/2014 | Foland | ............... | G06T 11/006 378/9 |
| 8,760,050 B2* | 6/2014 | Mohr | ............... | H05H 7/00 29/428 |
| 8,761,335 B2* | 6/2014 | Ishkhanov | ............... | H05H 7/12 378/119 |
| 8,774,351 B2* | 7/2014 | Funk | ............... | A61B 6/4488 378/62 |
| 8,803,453 B2* | 8/2014 | Eaton | ............... | H05H 7/02 250/492.3 |
| 8,885,975 B2* | 11/2014 | Yu | ............... | G06T 11/003 382/131 |
| 8,971,484 B2* | 3/2015 | Beckmann | ............... | G01N 23/046 378/62 |
| 9,025,024 B2* | 5/2015 | Xu | ............... | H04N 5/23206 348/142 |
| 9,052,265 B2* | 6/2015 | Holt | ............... | A61B 6/032 |
| 9,057,679 B2* | 6/2015 | Morton | ............... | G01N 23/04 |
| 9,167,681 B2* | 10/2015 | Cheung | ............... | H05H 7/02 |
| 9,257,253 B1* | 2/2016 | Allen | ............... | H01J 29/04 |
| 9,258,876 B2* | 2/2016 | Cheung | ............... | H05H 7/02 |
| 9,326,366 B2* | 4/2016 | Krasnykh | ............... | H05G 2/00 |
| 9,330,494 B2* | 5/2016 | Schultz | ............... | G06T 17/05 |
| 2003/0194053 A1 | 10/2003 | Schramm et al. | | |
| 2007/0183568 A1 | 8/2007 | Kang et al. | | |
| 2007/0274456 A1 | 11/2007 | Holt | | |
| 2009/0041185 A1 | 2/2009 | Might et al. | | |
| 2010/0310042 A1 | 12/2010 | Fox et al. | | |
| 2010/0310175 A1 | 12/2010 | Holt | | |
| 2011/0096083 A1 | 4/2011 | Schultz | | |
| 2011/0116596 A1 | 5/2011 | Sommer, Jr. et al. | | |
| 2011/0129066 A1 | 6/2011 | Statham et al. | | |
| 2011/0280440 A1 | 11/2011 | Holt | | |
| 2012/0106816 A1 | 5/2012 | De Man et al. | | |
| 2013/0076913 A1 | 3/2013 | Xu et al. | | |
| 2013/0101156 A1 | 4/2013 | Holt | | |

FOREIGN PATENT DOCUMENTS

| | | |
|---|---|---|
| JP | 2009-261519 | 11/2009 |
| WO | WO-2008/075595 | 6/2008 |

OTHER PUBLICATIONS

Holt, Kevin M., "Angular Regularization of Vector-Valued Signals", ICASSP 2011.

Srebro, Nathan et al., "Weighted Low-Rank Approximations", Proceedings of the Twentieth International Conference on Machine Learning (ICML-2003).

NPL Website, Published Aug. 31, 2007; http://www.classzone.com/books/earth_science/terc/content/investigations/esu101/esu101page05.cfm?chapter_no=investigation.

Alvarez, Robert E. et al., "Energy-Selective Reconstructions in X-ray Computerized Tomography," Phys. Med. Biol., vol. 21, No. 5, pp. 733-744; 1976.

Office Action dated Apr. 19, 2017 issued in U.S. Appl. No. 13/277,833.

Office Action dated Oct. 28, 2016 issued in U.S. Appl. No. 13/277,833.

Office Action dated Mar. 4, 2015 issued in U.S. Appl. No. 13/277,833.

Office Action dated Oct. 6, 2014 issued in U.S. Appl. No. 13/277,833.

Advisory Action dated Jun. 23, 2014 issued in U.S. Appl. No. 13/277,833.

Office Action dated Feb. 12, 2014 issued in U.S. Appl. No. 13/277,833.

Office Action dated Sep. 18, 2013 issued in U.S. Appl. No. 13/277,833.

* cited by examiner

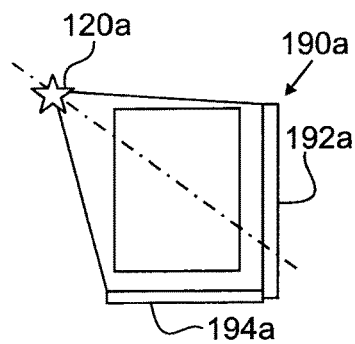
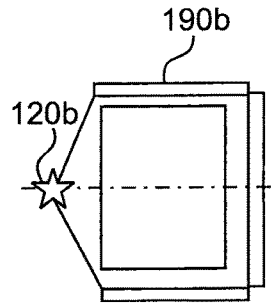
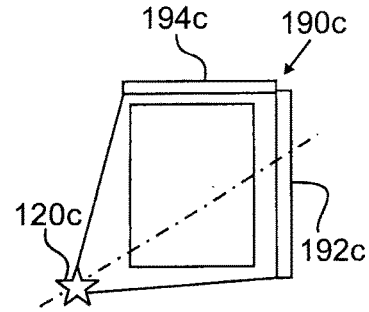
FIG. 4A  FIG. 4B  FIG. 4C
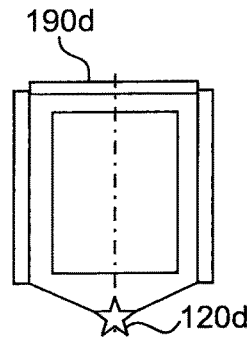
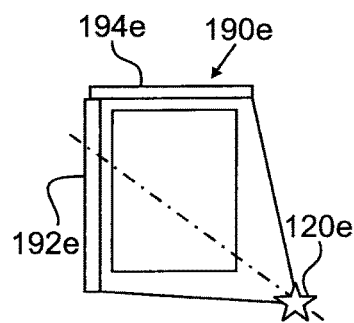
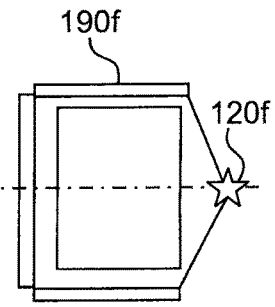
FIG. 4D  FIG. 4E  FIG. 4F
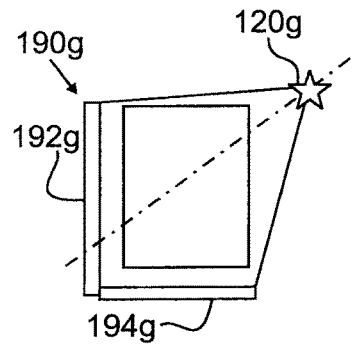
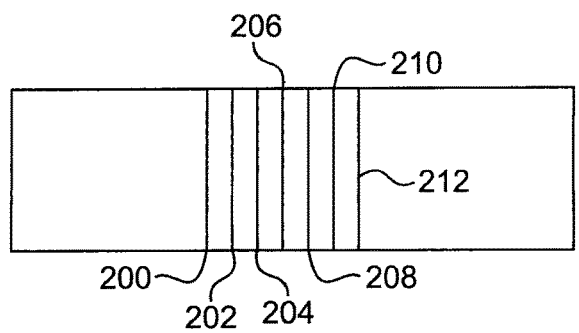
FIG. 4G  FIG. 5

SYSTEMS AND METHODS FOR MULTI-VIEW IMAGING AND TOMOGRAPHY

RELATED APPLICATION

The present application claims the benefit of U.S. Provisional Application No. 61/798,372, which was filed on Mar. 15, 2013, is assigned to the assignee of the present invention and is incorporated by reference herein.

The present application is related to U.S. patent application Ser. No. 13/277,833, which was filed on Oct. 20, 2011 and was published on Apr. 25, 2013 bearing U.S. Patent Publication No. 2013/0101156, is assigned to the assignee of the present application is incorporated by reference herein.

FIELD OF THE INVENTION

Radiation scanning of objects and, more particularly, radiation scanning of objects, such as cargo containers, by multiple sources, to reconstruct three-dimensional images.

BACKGROUND OF THE INVENTION

Radiation scanning systems used in cargo imaging technology, including land, sea, or air cargo, have advanced through multiple generations. First generation radiation scanning systems include gamma-ray sources, which are used in the mobile VACIS® gamma ray imaging system, available from Science Applications International Corporation, San Diego, Calif. ("SAIC"). The mobile VACIS® includes a Co-60 or Cs-137 isotope source and an array of individual NaI detectors operating in photon counting mode, mounted to a truck. Due to safety concerns and finite detector response time, source strength is around 1 Ci. Imaging resolution, penetration and contrast sensitivity are poorer than necessary. Typical penetration is 100 mm to 150 mm steel with ~15 mm display resolution (pixel size).

Second generation radiation scanning systems use single energy X-ray sources, such as the Varian M-series Linatrons, available from Varian Medical Systems, Inc., Palo Alto, Calif. The use of intense pulsed X-ray source and integration detectors greatly improved radiographic performance, such as resolution, penetration and contrast sensitivity. Steel penetration is over 400 mm with 3 mm resolution with an M6/Mi6 source. This allows an inspection to reveal most (two dimensional) details inside a cargo container.

Third generation scanning systems use dual-energy X-ray transmission radiography with material discrimination. In addition to superior radiographic performance, this generation of X-ray scanning systems provide pixel-by-pixel information of material classes, such as organic, inorganic, metallic and very high-Z metals. Algorithms may also be applied to smooth out material regions based on the fact that material types is not likely to change from pixel to pixel.

Fourth generation radiation scanning systems include dual-energy X-ray transmission radiography with stacked detectors and data fusion algorithms for enhanced material classification. While stacked detectors by themselves may not work well at MeV energies, they pick up material signatures at small beam path length, which complements information from dual source energies. Coupled with advanced algorithms, fourth generation radiation scanning systems can provide better material classification than the prior generations discussed above, and is useful with small beam path length as well as larger large objects.

FIG. 1 is a schematic representation of an example of a typical cargo radiography system 10. An electron accelerator 12, such as a Varian Mi6 Linatron® linear accelerator, available from Varian Medical Systems, Inc., Palo Alto, Calif., accelerates electrons from an electron source, such as an electron gun (not shown) and directs the accelerated electrons to the target 14. X-rays are produced at the target 14 and collimated by a collimator (not shown) into fan beams to image a slice of a cargo container 16. A linear detector array 18, which may have a curved profile or folded straight sections, for example, detects X-rays transmitted through the cargo container 16. A straight path from the X-ray source target 14 to each detector element of the linear detector array 18 forms a pixel in a resulting transmission image corresponding to each X-ray pulse. The linear detector array 18 records one column of pixels in a transmission image corresponding to each X-ray pulse. When the cargo container 16 moves through the fan beam (or the source-detector combination moves along the cargo container) and more image lines (columns) are detected, a complete 2-D transmission image is recorded. Each pixel contains integrated information along a beam path by a collimator (not shown) between the target 14 and each a detector element. In other words, information along each beam path is projected onto one pixel and is not recoverable from one radiographic view. With two or more radiation source energies, and optionally with stacked detectors, integrated material information along a beam path can be calculated. However, such material information is also projected along a beam path onto a pixel.

The linear detector array 18 is electrically coupled to an image processor 20, which is coupled to a display 22. The image processor 20 comprises analog-to-digital conversion and digital processing components, as is known in the art. A processing device 24, such as a computer, for example, is electrically coupled to and controls the operation of one or more of the electron accelerator 12, the linear detector array 18, a conveyor system (not shown), the image processor 20, and the display 22. One or more memory devices 26 to store a reconstruction algorithm, detected data, resulting images, etc., is also provided. Connections between the processing device 24 and of all the components are not shown, to simplify FIG. 1. The processing device 24 may be programmed to reconstruct 2-D images. The processing device 24 may provide some or all of the processing functions of the image processor 20. While one processing device 24 is shown, additional processors or computers may be provided, as well. The image processor 20, the processing device 24, and the display 22 may be arranged and connected differently. For example, the image processor 20 may be part of the processing device 24. The processing device 24 may be programmed in software and/or hardware.

FIG. 2 is a schematic representation of another example of a radiation scanning system 50, positioned to scan a cargo container 52 supported by a truck 54. A radiation source 56, a first collimator 58, a detector array 60, and a second collimator 62 are shown. The radiation source 56 comprises a source of electrons, an accelerator, and a target (not shown), as above. Radiation generated by the radiation source 56 is collimated by the first collimator 58 to form a fan beam or a cone beam. Radiation transmitted through the cargo container 52 and optionally the truck 54 are collimated by the second collimator 62 and detected by the detector array 60. The processing device 24, one or more memory devices 26, a conveyor system (not shown), the image processor 20, and the display 22 of FIG. 1 may be provided in the system 50 of FIG. 2, as well.

Conventional CT reconstruction typically requires hundreds or thousands of views. Filtered backprojection ("FBP"), or, more broadly, direct or analytic algorithms are commonly used to reconstruct CT images. Such algorithms are derived as analytic solutions to some idealized version of the actual problem to be solved. Two problem aspects that are commonly idealized are the geometry and the physics. Geometrically, most analytic algorithms assume that data are continuously sampled along an ideal arc or line. In terms of physics, most also assume an ideal X-ray imaging mechanism, such as a noise-free monochromatic infinitesimal-width pencil-beam from a point source with no scatter using perfect noise-free linear electronics, for example. Both of these assumptions are problematic.

SUMMARY OF THE INVENTION

Known fourth generation systems (dual-energy source with stacked detectors and algorithm) only provide projection images. Objects extending through an X-ray beam path are "squeezed" into a planar view. Except in a few simple cases, the 2-D image (with material information) may not contain sufficient information to resolve objects that overlap in a beam path direction. Furthermore, material information (atomic number or Z-value) is calculated for all materials along each beam path as a whole. This dilutes the material signature. A large piece of ordinary material will reduce the signature of a heavy metal along the same beam path.

In full scale X-ray tomography, projections, which are usually evenly spread, are taken around the cargo or other objects being examined. However, this typically requires rotating the whole X-ray source and detector assembly as one integrated piece, around the cargo container, or rotating the cargo container inside a tunnel defined by X-ray source and detectors. Mechanical complexity, scanning speed, and other practical concerns impedes its adoption. In full scale CT, an object is viewed at multiple angles, at small increments, typically over at least 180 degrees. Analytic reconstruction techniques, such as filtered back projection, may be used to resolve information along X-ray beam paths, for example. Known full scale CT proposals have not been practical for scanning large objects because of their complexity.

Embodiments of the invention aim to provide improved imaging of objects, including large objects such as cargo containers. Other embodiments of the invention provide quasi-three-dimensional image reconstruction from viewer views than in CT reconstruction.

In one embodiment, accelerated electron beams are transported to multiple targets at respective locations to generate X-rays for radiography of an object at different viewing angles. In one example, resulting 3-D images enhance the ability to identify the structural contents of cargo containers. In addition, material signatures may be resolved along beam paths, greatly improving specificity by decreasing dilution due to overlapping, for example. Improved structural and material information (Z-value) improves automatic feature and threat detection.

In another embodiment, a system collimates radiation generated by a plurality of radiation sources into multiple beams for scanning an object at multiple angles. The object may be a cargo container, for example.

As discussed above, CT reconstruction algorithms, such as filtered backprojection ("FBP"), assume that data are continuously sampled along an ideal arc or line. In terms of physics, most also assume an ideal X-ray imaging mechanism, such as a noise-free monochromatic infinitesimal-width pencil-beam from a point source with no scatter using perfect noise-free linear electronics, for example. Both of these assumptions are problematic.

However, when the detector pixels are unlikely to all fall on a convenient curve or line, or to be finely spaced enough to be considered nearly continuous, or when the number of views is small or not finely spaced enough to be considered nearly continuous, analytic algorithms are generally precluded. Instead, iterative algorithms are typically used. However, in addition to geometry, it can also be very useful to include a more realistic physics model into the reconstruction process. While conventional CT often requires a host of correction algorithms (for beam hardening, cross-talk, noise reduction, scatter, non-linear gain, streak removal, etc), many of these corrections are ad hoc and do not completely solve the problem. Furthermore, many such artifacts come about largely due to the mismatch between the actual physics model and the ideal model assumed by the algorithm. Therefore, by using a more realistic physics model many of the artifacts may be reduced or eliminated, and the need for many of the usual corrections may be obviated.

Another class of algorithms, generally called Statistical Reconstruction ("SR"), allows for not only a more complete physics model, but also models the characteristics of the noise and uncertainty in the imaging process. SR also allows for some prior knowledge of the object, FBP and the original ART methods may be thought of as very particular statistical models in which the logarithm of the pixel values have are assumed to have uniform Gaussian noise, and all reconstructed objects are considered to be equally likely. However, neither assumption is particularly realistic, because X-rays contain polychromatic Poisson noise, and detectors add further Gaussian noise (on the detected signal, not its logarithm). This may be unimportant when a large number of X-rays pass through the object, but when few photons make it through the object, using an accurate noise model becomes important.

Examples of models for different materials and feasibility criteria to reduce candidate materials to yield useful material-identification information are described in U.S. Patent Publication No. 2013/0101156 A1, which is assigned to the assignee of the present invention and is incorporated by reference herein.

In accordance with an embodiment of the invention, an algorithm is described to generate a quasi-3D image from a set of projection measurements from a plurality of radiation sources in a plurality of different planes. Embodiments of the invention enable quasi-3D image reconstruction from much less information then required in CT. For example, conventional CT might use hundreds or thousands of views, whereas in accordance with embodiments of the invention, meaningful quasi-3D images may be obtained from the order of 5 to 20 views, for example. More views may be used, if desired.

In accordance with an embodiment of the invention, a method of reconstructing images is disclosed comprising scanning an object by a first plurality of radiation beams generated by a second plurality of sources at a plurality of angles and detecting the first plurality of radiation beams. Images of the object are reconstructed from projection measurements by searching for an estimate of an image that optimizes an imaging model defining a likelihood of the estimated image underlying the measured data, and a feasibility model defining a likelihood that the estimated image occurs in nature. The estimate of the image may comprise material information.

BRIEF DESCRIPTION OF THE FIGURES

FIGS. 4A-4G shows examples of detector arrays that may be provided at each target station in the system of FIG. 3;

FIG. 5 shows examples of parallel imaging planes defined by each of the target stations and detectors of FIGS. 4A-4G;

DETAILED DESCRIPTION OF PREFERRED EMBODIMENTS

Multiple X-Ray Sources by Skewed Electron Transport

Figure 3:
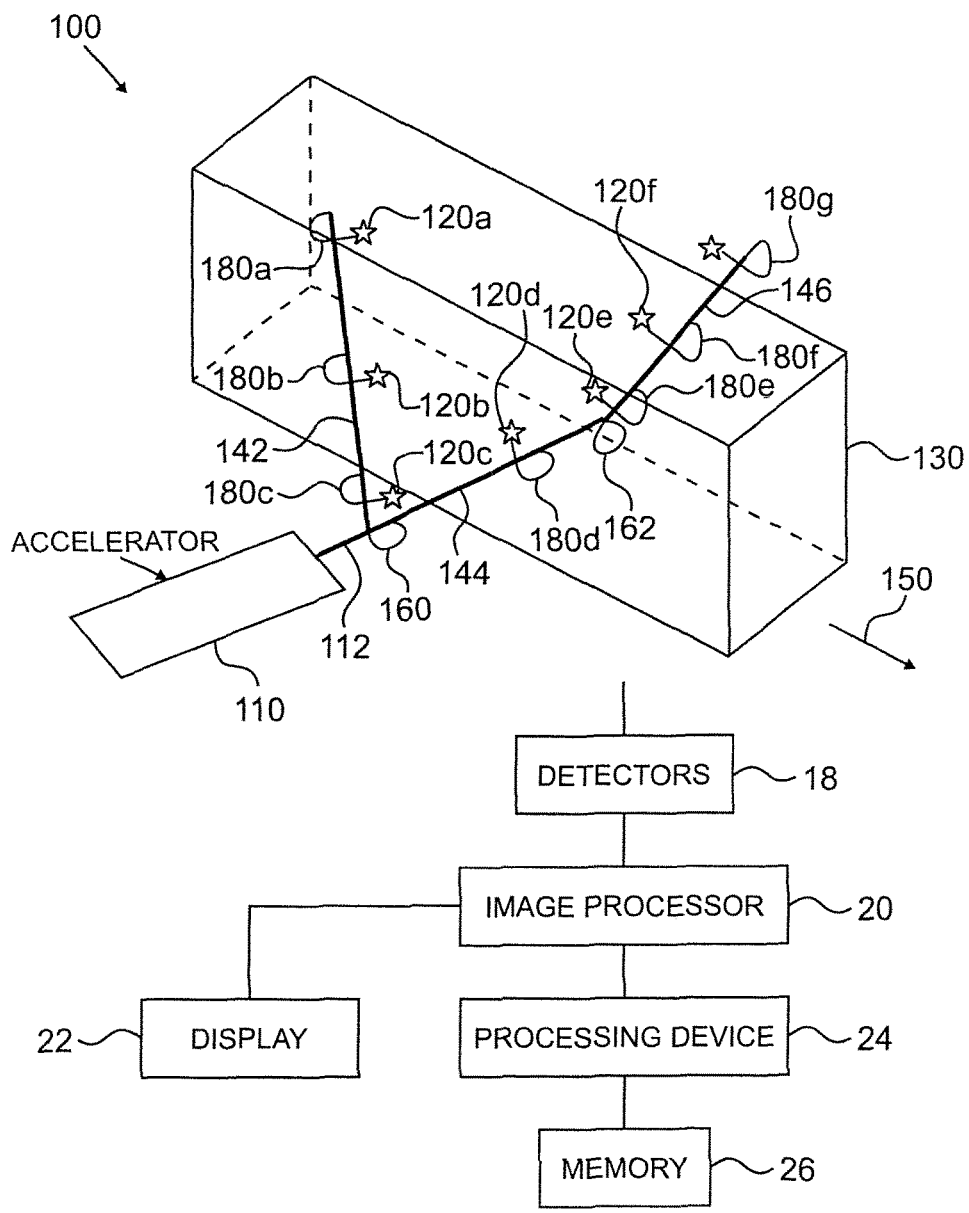
FIG. 3 is a schematic representation of a radiation scanning system in accordance with an embodiment of the invention.

FIG. 3 is a schematic representation of a radiation scanning system 100 ("system 100") in accordance with an embodiment of the invention. In this example, the radiation scanning system 100 comprises a single charged particle accelerator 110 ("accelerator 110"), such as an electron linear accelerator, and multiple X-ray target stations 120a-120g ("target stations 120a-120g") defining respective multiple viewing locations with respect to an object 130 to be examined. The object 130 may be a cargo container, cargo conveyance, or other object, for example. The electron linear accelerator may be a Linac, available from Varian Medical Systems, Inc., Palo Alto, Calif., for example. An accelerated electron beam, which is typically generated in short pulses, for example, is transported through electron beam transport pipes ("pipes") 142, 144, 146 and directed by magnetic fields to impact one of the multiple targets in the target stations 120a-120g to produce X-rays to scan the object 130 at different angles. An image processor 20, a display 22, a processing device 24, and memory 26, as described above with respect to FIG. 1, are also provided but not shown in this view. The processing device 24, the memory 26, the image processor 20, and the display 22 of FIG. 1 may be provided in the system 100 of FIG. 3, as well. In this example, the memory 26 may store a quasi-three-dimensional reconstructions algorithm, and components of the algorithm, as discussed below. In FIG. 3, the detectors or linear detector arrays 18 are indicated schematically as numeral 18. Examples of detectors used in this example are shown in FIGS. 4A-4G.

In the example of FIG. 3, the accelerator 110 supplies accelerated electrons to seven (7) X-ray target stations 120a-120g. More or fewer target stations 120a-120g may be provided. For example, five target stations may be provided. Each target station 120a-120g comprises a tube connecting an output of a respective electromagnet 180a-180g to the target within the target assembly (not shown). The target assembly comprises shielding, cooling tubes, and a mechanism to generate and/or maintain a vacuum, as is known in the art. The target may comprise tungsten and/or other high atomic numbers materials that generate a desired yield of X-ray radiation when impact by accelerated electrons by the Bremsstrahlung effect. The target may be a multi-layer target comprising tungsten and copper, for example, as is known in the art.

The object 130 may be moved through the radiation scanning system 100 continuously or in steps, during scanning by a conveying system 150 indicated schematically by an arrow. The conveying system 150 may comprise a conveyor belt, a movable platform driven by rollers, or a towing system, for example, as is known in the art. Alternatively, the accelerator 110 and target stations 120a-120g may be mounted to a gantry and moved with respect to the object 130, continuously or in steps.

Three electron beam transport pipes 142, 144, 146 are provided in this example to convey the accelerated electrons to each of the target stations 120a-120g. A pipe 142 is shown at the near side of the object 130 and runs upward; another pipe 144, which is aligned with the path 112 of the electron beam from the accelerator 110, runs beneath object and across to the far side of the object; and a pipe 146 runs upward at the far side of the object. There are three target stations 120a, 120b, 120c along the pipe 142: station 120a near the top of the pipe 142 and object 130, station 120b near the middle of the pipe 142 and the object, and station 120c near the bottom of the pipe and the object.

There is one target station 120d along the pipe 144, near a middle of the pipe. There are three additional target stations 120e, 120f, 120g along pipe 146: target station 120e near the beginning of the pipe, target station 120f near the middle of the pipe, and target station 120g near a top and end of the pipe. The pipes 142-146 are skewed so that the positions of the seven X-ray target stations 120a-120g are offset, to scan the object 130 in different imaging planes. The radiation beams may be separated by one to two feet. This facilitates the placement of collimators (not shown) and detectors 190a-190g. Examples of detector configurations are shown in FIGS. 4A-4G. Each target station 120a-120g defines an image beam plane parallel to each other and preferably perpendicular to the motion direction in which the cargo moves through the system 100 or the whole system 100 moves along the cargo. Alternatively, radiation beams may be collimated to be in different, parallel planes.

An electromagnet 160 is provided between the pipes 142 and 144. A second electromagnet is 162 is provided between the pipes 144 and 146. Electromagnets 180a-180g are also provided at each of the seven X-ray target stations 120a-120f. Appropriate electromagnets are known in the art and are routinely used in medical accelerators, for example, to bend accelerated electrons. Such electromagnets are referred to as "bend magnets." The electromagnets 160, 162, as well as the electromagnets 180a-180c, may be configured to bend the path of the electrons by 270°, for example. The electron beam pipes 142-146 are maintained at vacuum. Beam confinement and focusing can be applied along the pipes 142, 144, 146 to define a small electron beam spot as is also known in the art.

Detectors 190a-190g are provided on an opposite side of the object 130 as each target station 120a-120g, respectively, to detect radiation from each target station 120a-120g transmitted through the object 130, as discussed below and shown in FIGS. 4A-G.

Magnetic fields are applied by the electromagnets 160, 162, to steer a pulse of accelerated electrons along a respective pipe 142, 146, toward the target stations along the respective pipes. When a proper magnetic field is applied by the electromagnet 160, the pulse of accelerated electrons is steered into the pipe 142. When no magnetic field is applied to the electromagnet 160, accelerated electrons go straight into the pipe 144 which is aligned with the electron beam path 112. To steer a pulse of accelerated electrons from the end of the pipe 144 (if coming this way) into the entrance end of the pipe 146, a proper magnetic field is applied by the electromagnet 162 to the accelerated electrons travelling through the pipe 144. A proper magnetic field is also always applied at the target station 120g to steer accelerated electrons to the target station (if coming this way).

When an interlaced dual energy accelerator 100 is used, as described in U.S. Pat. No. 8,183,801 B2, which is assigned to the assignee of the present invention and is incorporated by reference herein, for example, electron orbits through an orbit chamber may be kept the same for the high energy pulses and low energy pulses. The higher energy electrons need a higher magnetic field to bend at the same radius as lower energy electrons. Magnetic field strength is controlled by adjusting electric current through the electromagnet, as is known in the art. The electric current may be controlled by a processing device, such as the processing device 24 in FIG. 1, for example. Alternatively, the excitation current need not be changed and the orbits of the electron beams at the different energies through the orbit chamber may be different, as described in U.S. Pat. No. 8,198,587 B2, for example, which is assigned to the assignee of the present invention and is incorporated by reference, herein. U.S. Pat. No. 8,198,587 B2 also describes a dual energy accelerator.

When a single energy accelerator 110 is used, accelerated electrons are cycled among the seven target stations 120a-120g. The following status Table A provides an example of magnet status for electron beam delivery to each target station 120a-120g. A blank means that its status does not matter, so the respective magnet can be on or off.

TABLE A

| Magnet 160 | On | On | On | Off | Off | Off | Off |
|---|---|---|---|---|---|---|---|
| Magnet 162 | | | | | On | On | On |
| Electrons to pipe | 142 | 142 | 142 | 144 | 146 | 146 | 146 |
| Magnet 180a | On | Off | Off | | | | |
| Magnet 180b | | On | Off | | | | |
| Magnet 180c | | | On | | | | |
| Magnet 180d | | | | On | Off | Off | Off |
| Magnet 180e | | | | | On | Off | Off |
| Magnet 180f | | | | | | On | Off |
| Magnet 180g | | | | | | | On |
| Electron to target | 120a | 120b | 120c | 120d | 120e | 120f | 120g |

When an interlaced pulse dual-energy accelerator is used, the accelerator produces a pulse of higher energy electrons followed by a pulse of lower energy electrons, to alternately generate high energy radiation and lower energy radiation. For example, when scanning cargo containers, the high energy may be 9 MeV and the low energy 6 MeV or the high energy may be 6 MeV and the low energy may be 3.5 MeV. The required magnetic field is different for steering high energy electrons and low energy electrons. One possible pulsing sequence is:

1. Directing a high energy pulse to pipe 142 and then to target station 120a;
2. Directing a low energy pulse to pipe 142 and then to target station 120a;
3. Directing a high energy pulse to pipe 142 and then to target station 120b;
4. Directing a low energy pulse to pipe 142 and then to target station 120b;
5. Directing a high energy pulse to pipe 142 and then to target station 120c;
6. Directing a low energy pulse to pipe 142 and then to target station 120c;
7. Directing a high energy pulse to pipe 144 and then to target station 120d;
8. Directing a low energy pulse to pipe 144 and then to target station 120d;
9. Directing a high energy pulse to pipe 144 and then to pipe 146 and then to target station 120e;
10. Directing a low energy pulse to pipe 144 and then to pipe 146 and then to target station 120e;
11. Directing a high energy pulse to pipe 144 and then to pipe 146 and then to target station 120f;
12. Directing a low energy pulse to pipe 144 and then to pipe 146 and then to target station 120f;
13. Directing a high energy pulse to pipe 144 and then to pipe 146 and then to target station 120g;
14. Directing a low energy pulse to pipe 144 and then to pipe 146 and then to target station 120g; and to scan the entire object or a desired portion of the object.
15. Repeat steps 1-14, above, for a desired number of cycles. Several hundred to several thousand cycles may be run.

As a result, a high energy radiograph and a low energy radiograph may be produced at each of the seven target stations 120a-120g. The number of radiographs doubles when two-layer stacked detectors 190a-190g are also used. Stacked detectors are described in U.S. Pat. No. 8,184,769, for example, which is assigned to the assignee of the present invention and is incorporated by reference herein. Radiographs from different X-ray target (source) stations 120a-120g have different viewing angles and may be used for image reconstruction, including tomographic reconstruction, to resolve information along X-ray beam paths (structural and material signature), as discussed further below.

While only one of the target stations 120a-120g is fired at a time, the pulsing sequence can run very quickly. For example when a 1,400 Hz accelerator is used, each X-ray target (source) station 120a-120g produces 100 high energy pulses and 100 low energy pulses per second.

FIGS. 4A-4G show examples of the multi-views provided in the example of FIG. 3, which enable cargo multi-view tomography. FIG. 4A shows the target station 120a and an L-shaped detector array 190a comprising first and second arms 192a, 194a. FIG. 4B shows the target station 120b on a U-shaped detector array 190b comprising first, second, and third arms 192b, 194b, 196b. FIGS. 4C, 4E, and 4G show the target stations 120c, 120e, 120g and L-shaped detector arrays 190c, 190e, 190g. The L-shaped detector arrays 190c, 190e, 190g each comprise first and second arms 192c, 194c; 192e, 194e; and 192g, 194g, respectively. FIGS. 4D and 4F show the target stations 120*d*, 120*f*. The U-shaped detector arrays each comprise first arms 192*d*, 192*f*; second arms 194*d*, 194*f*; and third arms 196*d*, 194*f*, respectively.

FIG. 5 shows an example of parallel imaging planes 200-212 defined by each of the target stations 120*a*-120*g*, respectively.

As shown in FIGS. 4A-4G, radiographs are taken at different viewing angles, as the object 130 is moved through the system 100, satisfying the fundamental requirement of tomographic reconstruction. At each location of the object 130 where scanning takes place, each radiograph provides a projection view of a slice of the object 130, resulting in a line (column) in the corresponding radiograph. At a particular location of the object 130, each target station 120*a*-120*g* and corresponding detector array 190*a*-190*g* images a different parallel slice of the object. After the object 130 moves through the radiation scanning system 100, imaging at each target station 120*a*-120*g* provides a complete 2-D projection radiograph of the object. The seven radiographs are then shifted along the scanning motion direction to align slice positions, based on knowledge of the physical location of the seven image planes 200-212. At this point, seven radiographs of the object 130 from seven viewing angles are aligned as if they were taken simultaneously at a single location and plane.

When an interlaced-pulse dual-energy accelerator 110 is used, the accelerator sequentially produces a pulse of higher energy electrons followed by a pulse of lower energy electrons at each target station 120*a*-120*g*. Slices of the object 130 are imaged at least twice at each X-ray target station 120*a*-120*g*, or from each viewing angle, at least once for each energy. All seven high energy radiographs are assembled into a high energy radiograph data set and all seven low energy radiographs are assembled into a low energy radiograph set. The number of radiograph sets doubles when two-layer stacked detectors are used, as discussed above. The interlaced accelerator may be a Mi6 Linatron® that generates radiation at 3.5 MeV and 6 MeV, or an Mi9 Linatron® that generates radiation at 6 MeV and 9 MeV, both available from Varian Medical Systems, Inc., Palo Alto Calif., for example. Three or more energies may be interlaced, as well. In addition, any number of layers may be provided in the stacked detectors.

Since the seven radiographs within any data set from different X-ray target stations 120*a*-120*g* have different viewing angles, they may be used for tomographic reconstruction to resolve structural and/or material information along the X-ray beam paths. One radiograph set (usually the high energy set for best quality) may be used to reconstruct a 3-D object distribution, slice by slice in this configuration, with a quasi 3-D reconstruction algorithm, for example. With structural information about the object 130, other radiograph sets may be used to further resolve material information (effective atomic number, Z value, or similar quantity) of each voxel. An example of a procedure quasi 3-D reconstruction algorithm for resolving this non-additive quantity is described below. Other reconstruction algorithms may be used, as well. While tomographic reconstruction may be provided, it is not required.

In-Plane Multiple X-Ray Sources by Electron Transport

Figure 6:
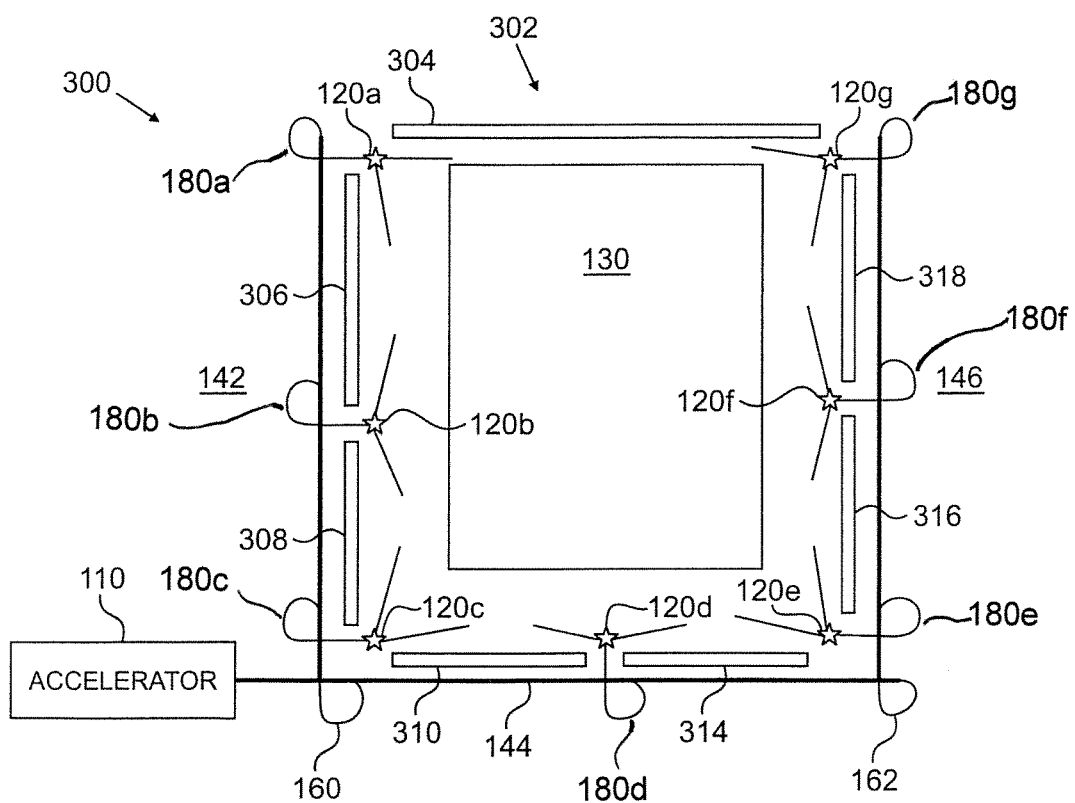
FIG. 6 is an example of a radiation scanning system in accordance with another embodiment of the invention, in which in-plane electron transport and a single, wrap-around detector array is provided for all the target stations.

FIG. 6 is an example of a radiation scanning system 300 ("system 300") in accordance with another embodiment of the invention, in which in-plane electron transport and a single, wrap-around detector array 302 is used for all target stations 120*a*-120*g*. Components common to the example of FIG. 3 are commonly numbered. Seven target stations 120*a*-120*g* are provided, as in the embodiment of FIG. 3.

The detector array 302 and the target stations 120*a*-120*g* surround the object 130 in a single plane. The processing device 24, the memory device 26, the image processor 20, and the display 22 of FIGS. 1 and 3 may be provided in the system 300 of FIG. 6, as well. A conveying system (not shown), may be provided to move the object 130 through the radiation scanning system 300 or the scanning system 300 may be mounted on a gantry for movement over the object 130, as discussed above.

Pipes 142, 144, 146 are provided, positioned adjacent to the same surfaces of the object 130, except that they lie in the same plane. The pipe 144 is aligned with the path 112 of the electrons output from the accelerator 110. The electromagnets 160 allows the accelerated electrons to proceed to the pipe 144 or directs the accelerated electrons to the pipe 142. The electromagnet 162 directs accelerated electrons through the pipe 146. Electromagnets 180*a*-180*g* direct accelerated electrons to the respective target stations 120*a*-120*g*. The detector array 302 comprises detector array sections 304-318, all lying in the same plane. Spaces are provided between adjacent detector array sections 304-318, respectively, to provide paths for the accelerated electrons bent by the electromagnets 180*a*-180*g* to the target stations 120*a*-120*g*, respectively, as shown in FIG. 6.

At least a portion of all of the detector array sections 304-318 will detect radiation transmitted through the object 130 from each target station 120*a*-120*g*. Since only one target station 120*a*-120*g* works at one time, they are using the detectors in a time-sharing arrangement.

Integrating Out-of-Plane Scatter Detector

In one example, X-ray radiation generated from a respective target station 120*a*-120*g* is collimated into a fan beam. X-rays interact with the material in the object 130 along its beam path with a probability of interaction dependent on material type, material amount, and X-ray photon energy. Scattered X-ray photons travel along a path different from the original beam path. Most of scattered X-ray photons will travel out of the plane defined by the source collimator (not shown) and detectors 190*a*-190*g*, resulting in out-of-plane scatter. In addition, some X-ray photons will take a new path within the plane defined by source collimator and detectors 190*a*-190*g* resulting in in-plane scatter. While the mixture of scattered X-rays with non-attenuated X-rays (those that pass through the object 130 without interaction), may deteriorate imaging performance, scattered X-rays carry supplementary information about the object 130 that may be useful in image reconstruction if the scattered X-rays are recorded separately.

Figure 7:
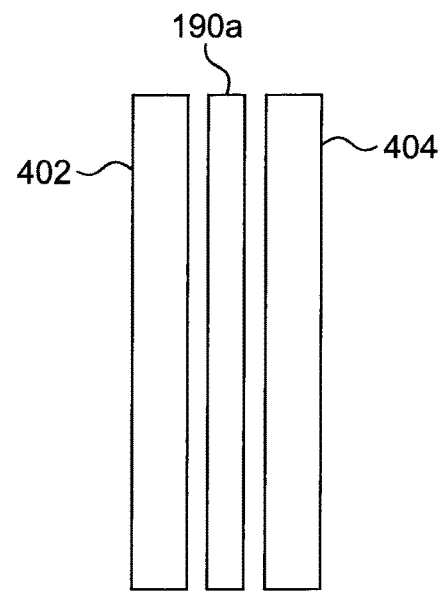
FIG. 7 is an example of scatter detector arrays adjacent to a leg of a detector array in FIG. 4.

In accordance with an embodiment of the invention, out-of-plane scatter detector arrays provided adjacent to the transmission detector arrays 190*a*-190*g* to record out-of plane scattered X-rays, such as slightly out of plane scattered X-rays. FIG. 7 is an example of scatter detector arrays 402, 404 adjacent to a leg of the detector array 190*a* of FIG. 4A. Scatter detector arrays 402, 404 may be provided adjacent to any or all of the legs of the detector array segments 190-190*g*. A single scatter detector array may be provided on one side of some or all of the transmission detector arrays 190*a*-190*g*, as well. Backscatter detectors may also be provided, proximate the target stations, for example. Backscattered radiation and forward scattered radiation may be considered separately.

In one example, a proportion of the radiation recorded by the scatter detectors 402, 404, is subtracted from the radiation recorded by the respective detectors 190*a*-1190*g*, which detect radiation transmitted through the object 130.

Information from scatter detectors may be combined with that from transmission detectors and used in reconstruction algorithm by the processing device of the radiation scanning system 100, as discussed herein.

In-Plane Scatter Management with Rotating Detector Modulators

Figure 8:
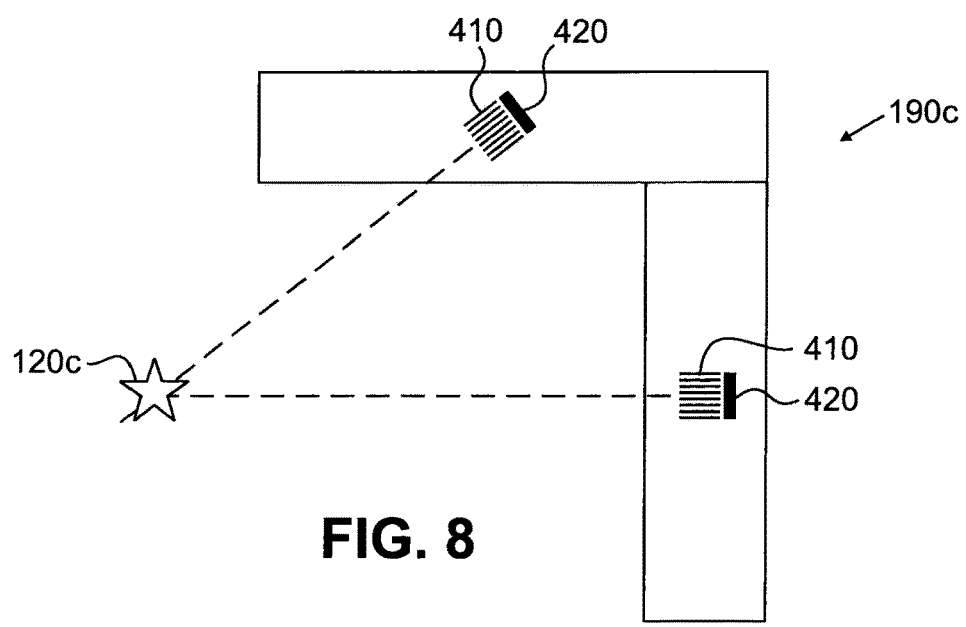
FIG. 8 is an example of a modification to transmission detector array in FIGS. 4A-4G that may be used in the skewed implementation of FIGS. 3 and 4, for example.

FIG. 8 is an example of a modification to the transmission detector array 190*c* that may be used in the skewed implementation of FIGS. 3 and 4A-4G, for example, in which each target station 120*a*-120*g* has its own detector array 190*a*-190*g*, respectively. Collimator vanes 410 may be incorporated to reject in-plane scattered X-rays for improved imaging performance. The imaging detectors in the detector array 190*c* are grouped into detector modules 420 and the collimator vanes 410 are added to the detector modules 420. The detector modules 420 are rotatable in the detector array 190*c* to face toward the respective target station, such as target station 120*c* in FIG. 8. The detector modules 420 are fixed in the position facing the respective target station 190*a*-190*g*. An example of the use of collimator vanes 410 with detector modules 420 fixed in position facing a target station may be found in the Varian IntellX® gantry systems, available from Varian Medical Systems, Inc., for example. The vanes may be rotatable, as well.

Figure 9A:
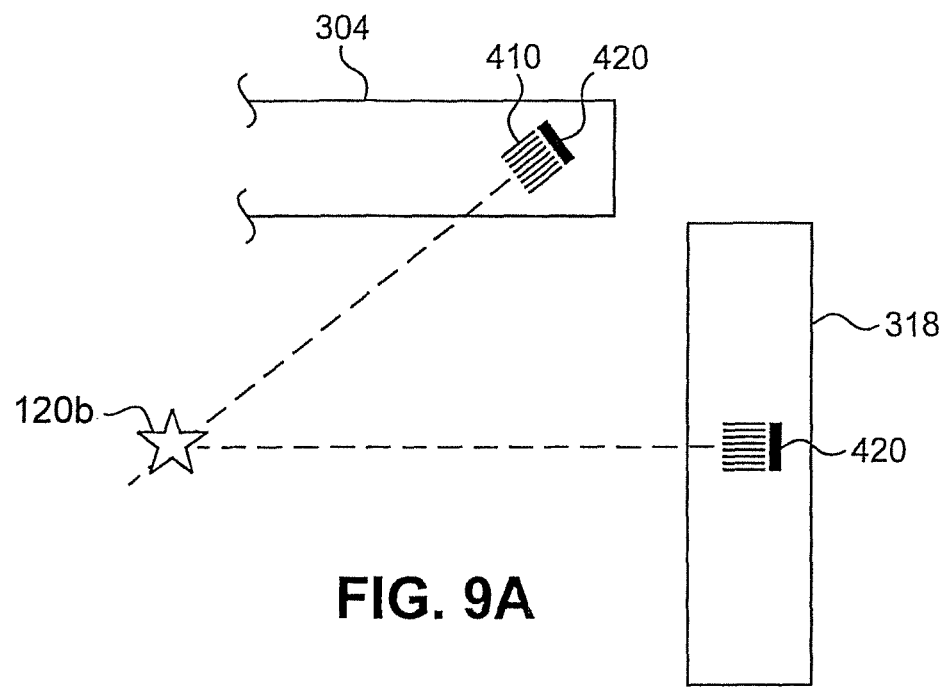
FIGS. 9A and 9B are examples of detector modules aimed at different sources, in the embodiment of FIG. 6.
Figure 9B:
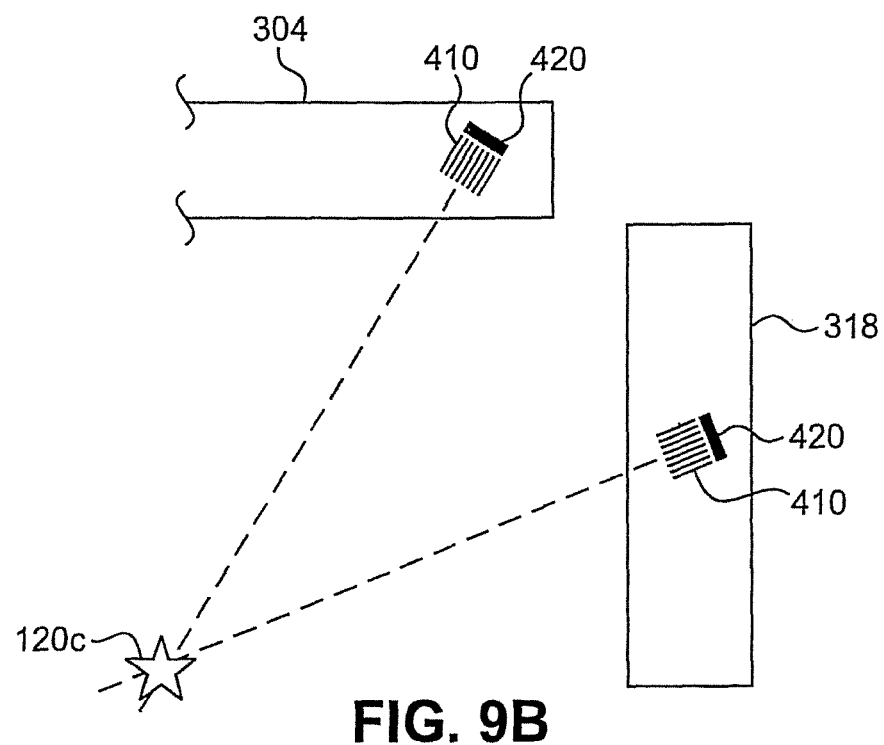

As mentioned above, with in-plane multiple X-ray sources, such as in the scanning system 300 of FIG. 6, radiation emitted by all of the target source stations 120*a*-120*g* may be detected by at least portions of all of the detector array section 304-316. The beam paths from various source stations 120*a*-120*g* to a specific detector element are therefore different. To accept direct transmission X-rays from all the target stations 120*a*-120*g* sequentially, after recording signals detected from one target station, the detector modules can be rotated about a pivot to point to the next target station in the sequence. This dynamic collimation is demonstrated in FIG. 9A and FIG. 9B, which show detector modules 420 in the detector array sections 304, 318 from FIG. 6. In FIG. 9A, the detector modules 420 are aimed toward the target station 120*b*, and in FIG. 9B the detector modules 420 are aimed toward the target station 120*c*. The detector modules 420 may be rotated by motors (not shown), for example, under the control of the processing device of the radiation scanning system 300.

Scatter detectors may be provided in this embodiment, in a similar manner as discussed above with respect to FIG. 7. The same set of scatter detector can operate as backscatter detectors for active sources and forward scatter detector for inactive sources.

The locations of target stations 120*a*-120*g* are examples and the stations may be located in other positions around the object 130 being scanned. In some examples, only two pipes may be provided.

While in these examples only one accelerator used to provide accelerated electrons to all the target stations 120*a*-120*g*, additional accelerators may be provided to provide accelerated electrons to at least two respective target stations. In this way, there are still fewer accelerators than target stations, saving costs.

Although straight detector arrays are shown in the description, curved detector arrays may be provided. Different pulse sequences (of energy and target station) other than the one described may also be used—as long as it covers all source stations and all energies in one cycle.

Quasi-3D Reconstruction

In accordance with another embodiment of the invention, quasi-3D image reconstruction is provided from a set of projection measurements resulting from radiation scanning of an object from a plurality of views by a respective plurality of radiation sources. These possibilities are referred to as quasi-3D imaging herein. The quasi-3-D reconstruction algorithms may be conducted by the image processor and the processing device of the scanning system, for example. The end result of a 3-D reconstruction algorithm shown to the user can be one of several forms:

- a 3D isotropic volume with cubic voxels, for example, similar to modern medical imaging (full 3D);
- a 3D anisotropic volume with resolution much better in one dimension than another;
- a set of 2D image slices at different locations, optionally at coarse locations (where spacing between slices is much larger than pixel spacing), for example; and
- a single 2D image slice whose location can be manipulated (rotated, slid, nudged, etc).

Embodiments of the invention provide a more accurate geometric description of the scanning system, as well as a more realistic physics model, into the reconstruction process. Using feasibility information and prior knowledge of an object can also be useful. If the radiation scanning system itself does not generate much information, such as with an impenetrable X-ray path or a noisy scanner, there may be many images that are consistent with the scanner's projection data. However, many of those images might not be physically realistic. By narrowing choices down to those images that are physically likely, much less information is required from the scanning system. This observation has enabled new imaging methods, such as compressed sensing, and is also fundamental to recent advances in limited view CT reconstruction, especially for medical imaging in cases where human anatomy is well known and previous images of the same patient might also be available.

Figure 10:
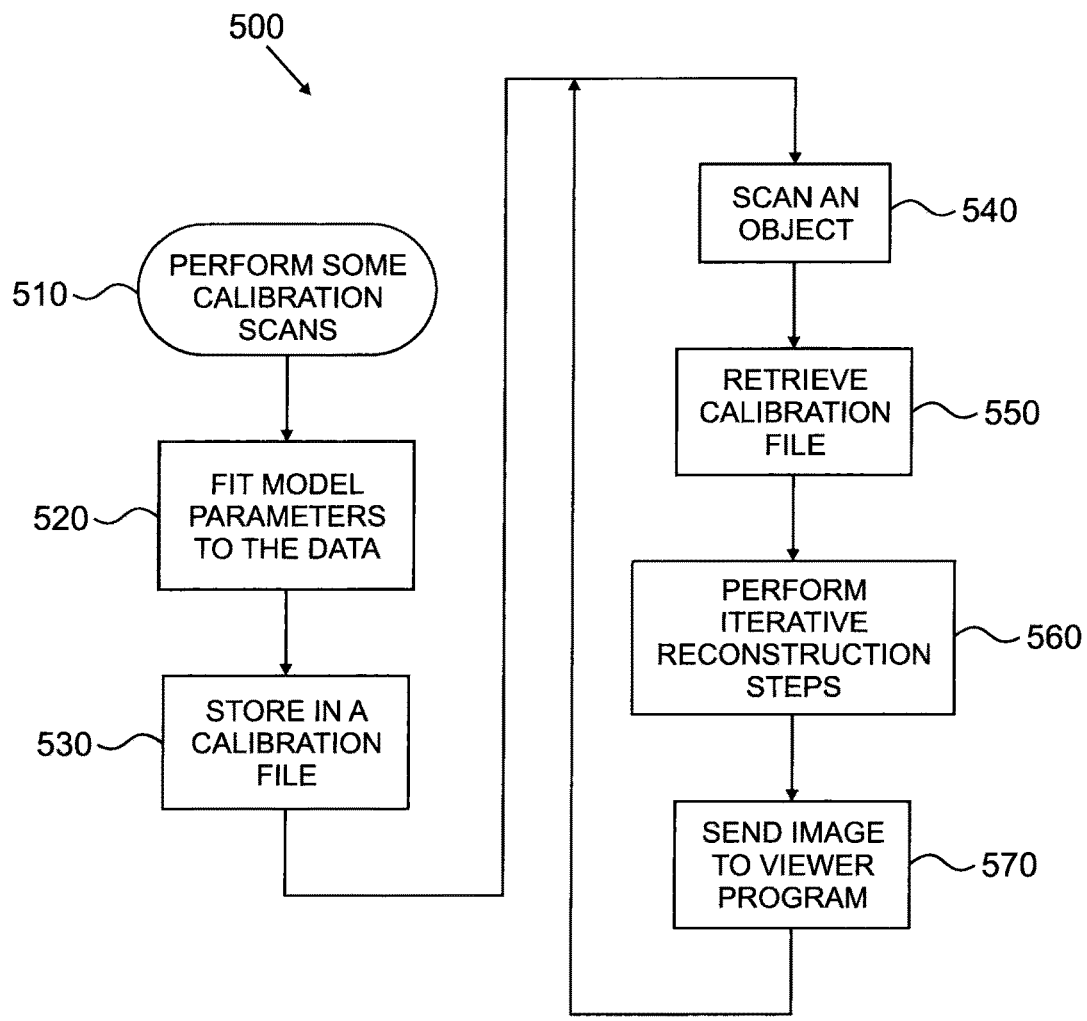
FIG. 10 is a flowchart of an example of the operation of a radiation scanning system, including image reconstruction in accordance with an embodiment of the invention.

FIG. 10 is a flowchart 500 of an example of the operation of a radiation scanning system, such as the radiation scanning system 100 described above and the radiation scanning system 800 described below. Calibration scans are performed in Step 510, as is known in the art.

Model parameters related to the radiation scanning system are fit to the data, in Step 520. Model parameters may include the spectrum of the radiation beams and the geometry of the radiation scanning system, such as the geometrical relationship between the radiation sources, the detectors, and the object being examined, for example. The spectrum may be determined as described in U.S. Pat. No. 8,983,234, which was filed on Sep. 28, 2012, is assigned to the assignee of the present invention, and is incorporated by reference herein, for example. The geometrical relationship between the radiation source, the detectors, and the object 130 being examined may be determined as described in U.S. Pat. No. 7,922,390 B2 and U.S. Pat. No. 9,052,265, which are also assigned to the assignee of the present invention and are incorporated by reference herein, for example. The model parameters are stored in the calibration file, in Step 530.

The object is scanned, in Step 540, the calibration file is retrieved, in Step 550, and iterative reconstruction is performed in accordance with embodiments of the invention, in Step 560, as described below. A reconstructed image is provided to a viewer program, in Step 570, and scanning of the object continues in Step 540.

Figure 11:
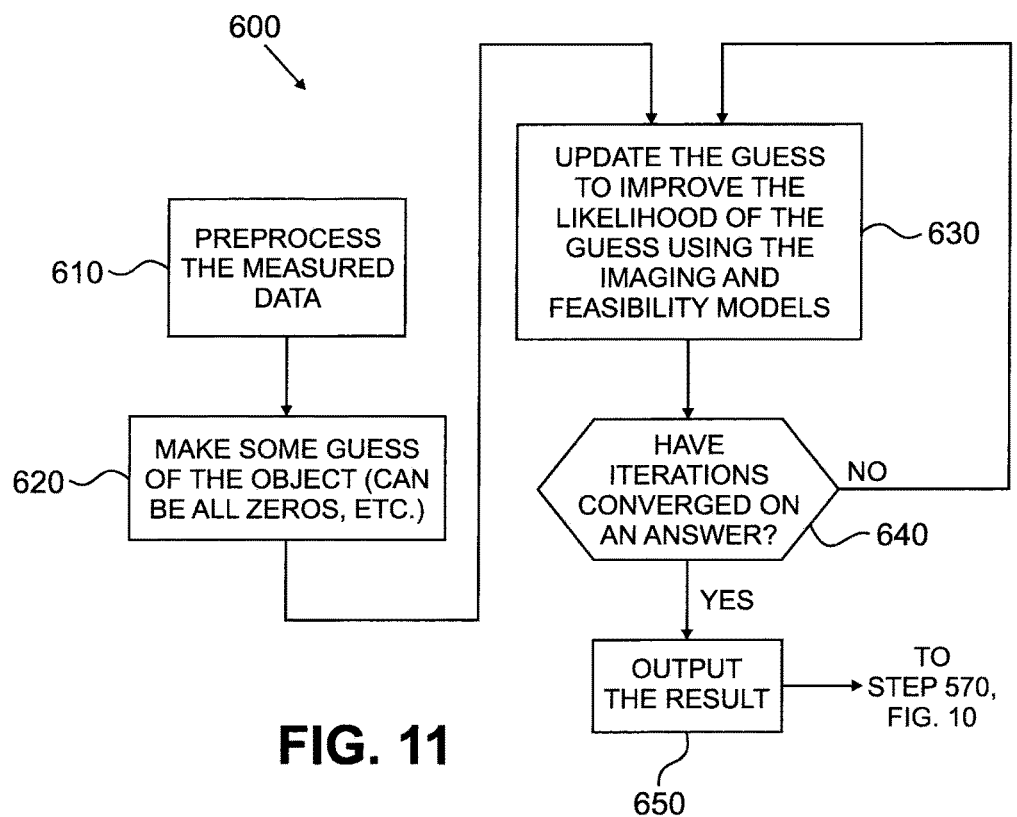
FIG. 11 is a flowchart of an example of an iterative reconstruction procedure in accordance with an embodiment of the invention, that may be used in FIG. 10.

FIG. 11 is a flowchart of an example of an iterative reconstruction procedure 600 (Step 560 of FIG. 10), in accordance with an embodiment of the invention. Measured data is preprocessed, in Step 610. An initial estimate or "guess" is made of the object, in Step 620. The guess may be all zeros, for example. The guess is updated to improve the likelihood of the guess, using imaging and feasibility models, in Step 630. This may be determined based on a cost function, for example, as discussed further below. It is determined whether the current guess has converged on an answer, in Step 640. If not, the method returns to Step 630 to update the guess. If Yes, then the answer is output, in Step 650, and the image is sent to the viewer program, in Step 570 of FIG. 10.

Figure 12:
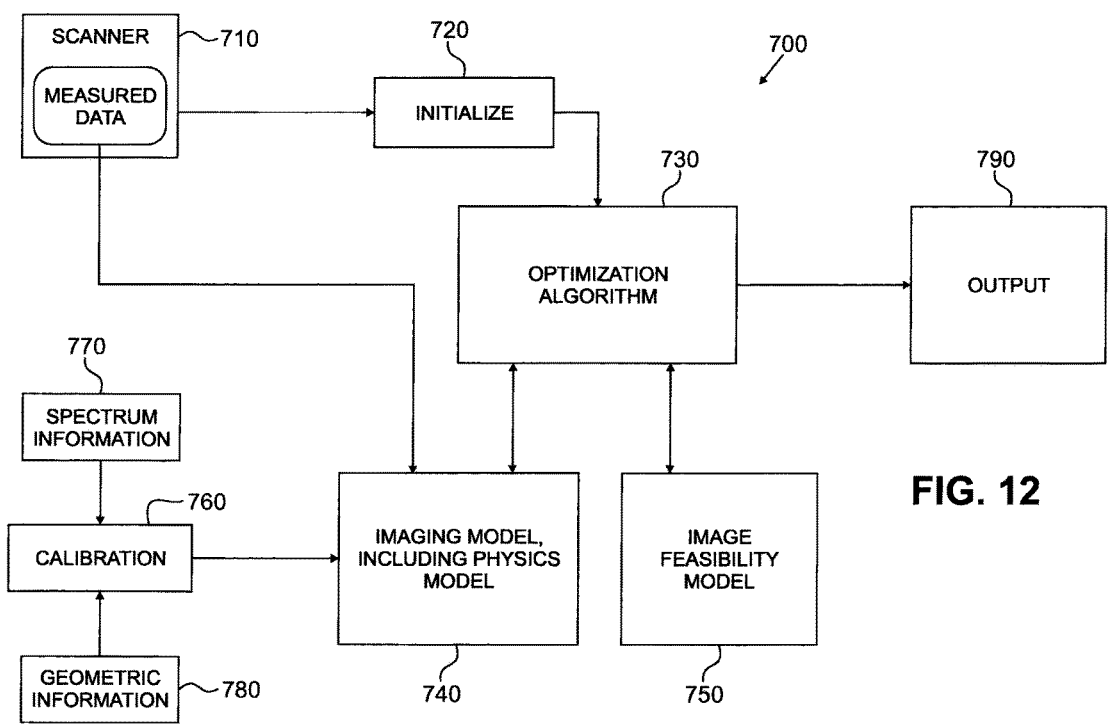
FIG. 12 is a schematic diagram of an example of the components of a reconstruction algorithm in accordance with an embodiment of the invention.

FIG. 12 is a schematic diagram of an example of the components 700 of a reconstruction algorithm in accordance with an embodiment of the invention. The radiation scanning system and data collected in the scanning procedure are indicated by numeral 710. The measured data is a set of measurements that represents a projection of the image to be recovered. Initialization 720 refers to the first guess (Step 620, FIG. 11).

The optimization algorithm 730, in accordance with an embodiment of the invention, receives the initial guess. The optimization algorithm 730 searches for an underlying image that is most likely based on the imaging model 740 and the image feasibility model 750. The imaging model 740 describes how likely it is that measured data would have been collected, based on the current guess. The imaging model 740 is based, at least in part on a physics model related to all materials or to particular materials of interest, as discussed below. The imaging model 740 is also based on the calibration 760, which receives as inputs spectrum information 770 and the geometric information 780, described above. The image feasibility model 750 describes how likely it is that a given guess about an image can occur in nature, regardless of what is measured. These components are discussed in more detail below. The optimization algorithm 730 provides an output 790, which corresponds to Step 650 in FIG. 11.

In security scanning, one might know many things about the objects being scanned. Some possibilities, referred to as feasibility criteria or "Regularization Options," include:

1. Density will never be negative;
2. Density will rarely exceed a first limit and will never exceed a second limit. For example, the density will rarely exceed 10 g/cm$^3$ (density of typical machinery) and presumably will never exceed 22.5 g/cm$^3$ (the density of Osmium, which is the heaviest element) typically transported;
3. Density is often piecewise smooth or piecewise constant (spatially);
4. Many objects have sparse representations using some dictionary, including a standard dictionary such as wavelets or curvelets, or a custom dictionary (for trucks, for example);
5. Many objects have regions that look very similar to other regions within the same object;
6. The material composition of an object is often piecewise constant (spatially);
7. Many parts of an image of an object taken on one day may look very similar to an image of the exact same object taken on another day;
8. An appearance of an object, such as a truck when empty may be known based on the make and model of a truck that is being scanned, and what that typically looks like in an image (when empty);
9. Materials have some expected frequencies and relationships:
    a. plastic, steel, brass, aluminum, carbon, organics are very common;
    b. some materials (like alkalis and halogens) are not stable by themselves, and usually appear only in some minimum ratios with compatible complementary elements;
    c. some materials (like rare earths) are very unlikely to be present except in very small quantities; and
    d. some materials (like Darmstadtium and other very heavy elements) have a half-life so small that they are essentially impossible to find inside a cargo container.

Of these:
  i. items 1-5, 7, 8 are applicable regardless of whether single-energy or multi-spectral scanning is used;
  ii. items 6 and 9 require multi-spectral (two or more spectra and/or stacked detector);
  iii. items 1, 3, and 4 are common in iterative CT reconstruction (especially low-dose or limited view);
  iv. item 5 is similar to non-local-means regularization, which is a well known technique for conventional image denoising;
  v. items 6 and 9 were described in the Non-Invasive Identification patent application (which is incorporated by reference herein and is identified further, below); and
  vi. items 7 and 8 may be based on known medical imaging methods. In particular, item 8 may be based on atlas methods, and item 7 may involve re-using prior scans (say, from a different modality, or the same or similar modality from a day or a month prior, for example).

In an example of an embodiment of the invention, a reconstruction algorithm performs the following steps:

1) Define P as the projection data acquired by a scanning system. Such as the scanning systems described herein or other scanning systems;
2) Define X as the quasi-3D image to be reconstructed;
3) Define D(X,P) as the data term, which is smaller when P and X are consistent, and larger when they are not;
4) Define R(X) as an unlikelihood term. It is smaller when X is reasonable, and larger when X is physically unlikely. When we are using several different types of prior knowledge, we may have several such functions $R_1, R_2, \ldots$;
5) Each unlikelihood term $R_n$ is assigned some penalty weighting $\lambda_n$; and
6) Define C(X,P) as our reconstruction score, where $C(X,P)=D(X,P)+\Sigma_n \lambda_n R_n(X)$. Then the reconstruction algorithm searches for the value of X that minimizes C(X,P).

Geometric Description

The geometric description discussed above with respect to Step 520 of FIG. 10 and item 780 of FIG. 12 defines the discussed above and is known in the art. In one example, j may be the coordinate(s) of a datum within the projection data. For example, with multiple line-arrays each with multi-layer detectors, and multiple sources each with multi-spectra, j would be the tuple (channel, view, detArray, detLayer, srcIdx, srcEnergy). Given j, there is some vector r(j) that describes the path covered by that X-ray.

Typically, i=(x,y,z), where i is the coordinates of some reconstructed pixel or voxel X(i).

The amount of overlap of ray j and voxel I, may be described by v(i,j). Usually this is calculated as a volume, but it could alternately be a path length or a volume fraction.

Output Representation

The output of Step 650, FIG. 6, described in Step 2, above, may be X(i), which is a tensor field. That is, each voxel contains a K-dimensional material description. When using single-energy imaging, then typically K=1 and X(i) represents density. For multiple spectra, using multiple X-ray energies and/or a stacked detector, as described in U.S. Patent Publication No. 2013/0101156 A1, which is assigned to the assignee of the present invention and is incorporated by reference herein, and mentioned above, this number will usually be larger than one for single-energy imaging in order to represent the material content at each location. There are two ways to represent X:
- separate-spectrum
- material-descriptors Separate-Spectrum Representation One possibility is to essentially make a separate quasi-3D reconstruction for each spectrum. That is $X_k(i)$ is the product of (average volume density in voxel i) with ($\mu_k^{avg}$=average mass attenuation coefficient or the linear attenuation coefficient in spectrum k).

In this case, if the image is X then we would expect datum j to have a value similar to $$Q(j, X) = e^{-\Sigma_i v(i,j) X_k(i)}$$

where k is the effective spectrum used in ray j.

It may be useful to estimate density from X. Typically this is done by weighted average $$\rho(i) = \sum_k w_k X_k(i) / \mu_k^{avg}$$

where $w_k$ is some set of weights that sums to one.

This approach is also useful when there is only a single spectrum.

Material-Descriptors Representation

X may more directly characterize the materials. For megavolt cargo imaging the space of all possible materials appears to have a dimension around 3 to 5. If multiple spectra are used, K>5 may not help and K<3 may not capture all material information present in the imaging data. In one example K=4 may be used, for example.

A material model maps a material description to a corresponding interaction inside the physics model. In particular, it is useful for the material model to allow calculation of an approximate attenuation curve for a particular material. For a suitable set of basis functions, the approximate attenuation curve for voxel X is:

$$\mu(i, E) = \sum_{k=1}^{K} A_k(E) X_k(i).$$

For a good set of basis functions and K≥4, in general for any real material, there is some choice of X(i) that makes the approximate attenuation curve very similar to the real attenuation curve. Such basis functions can be designed by a number of techniques. As described in U.S. Patent Publication No. 2013/0101156 A1, which is assigned to the assignee of the present invention and is incorporated by reference herein, one such technique is to form a matrix of mass attenuating values across all elements in the periodic table (or only elements of interest), in one matrix dimension and all energies of interest in another matrix dimension. A singular value decomposition ("SVB") may then be performed on the matrices, and the largest singular vectors, such as the largest three singular vectors, the largest four singular vectors, or the largest five singular vectors, are kept. As is also described in U.S. Patent Publication No. 2013/0101156 A1, weighted SVD ("WSVD") may also be performed, whereby energies are weighted by flux and detector sensitivity, materials are weighted by importance, and/or combinations of energy and material are weighted by expected transmission. WSVD is also described in "Weighted Low-Rank Approximations" by Srebo et al., in the Proceedings of the Twentieth International Conference on Machine Learning (ICML-2003), which is incorporated by reference herein.

A useful physics model (referred to in item 740 in FIG. 12, for example), is that as photons of energy E in ray j pass through voxel i, they are attenuated by a factor of $e^{-v(i,j)\mu(i,E)}$. Therefore we expect the detector for datum j to have a value like:

$$Q(j, X) = \int \phi(j, E) e^{-\Sigma_i \Sigma_{k=1}^{K} v(i,j) A_k(E) X_k(i)} dE$$

where $\phi(j,E)$ is the estimated spectrum for datum j. This can be known from the mechanical design, Monte Carlo simulation, or from a calibration method. Other Q functions can also be used (for example, if $\phi$ is too difficult to estimate, or the above model is not realistic enough). Other options include finding Q empirically as a function of X, during a calibration step, or using an analytic model (similar to the above) but modified to be either more realistic (perhaps more complicated) or to be easier to work with. In any case, the imaging model measures whether the measured data and the estimated data are both consistent with the physics model.

It is more complicated to estimate density from X in this version. Several options include:

$$\rho(i) = \|X_k(i)\|$$

$\rho(i) = FX_k(i)$ for some appropriately designed matrix F or $\rho$ might be a more complicated nonlinear function. When choosing the A bases, one may choose bases in such a way that one of these density estimates is more accurate and/or more tractable.

Data Term

The imaging model can be enacted via a data term that compares P and Q. Using likelihood estimation (regardless of the Q calculating method), the data term (Step 3, above), is:

$$D(X) = \sum_j \alpha_j (Q(j, X) - P(j) \log Q(j, X)),$$

which can be derived as the −log of the probability that we would have measured P given that we expected to measure Q and that our measurements are dominated by Poisson statistics. α is an optional weight that indicates the SNR of the spectrum associated with ray j (usually it is best to set this equal to the average effective number of photons through air, which can be estimated as $\alpha=SNR^2$ where SNR is measured in ray j through air).

There are also other alternatives for D. For example, a comparatively simple method is the simple least squares:

$$D(X) = \sum_j \alpha_j (Q(j, X) - P(j))^2;$$

or least squares of logarithms:

$$D(X) = \sum_j \alpha_j (\log Q(j, X) - \log P(j))^2$$

For example, using least squares of logarithms, together with the "Separate-Spectrum" representation essentially leads to the basic ART algorithm.

Prior Knowledge

Regularization Option #1 can be expressed for separate-spectrum as $$R(X) = \begin{cases} 0, & \text{if } X_k(i) \geq 0 \text{ for all } i, k \\ \infty, & \text{if } X_k(i) < 0 \text{ for any } i, k \end{cases}$$

or for material-descriptors as $$R(X) = \begin{cases} 0, & \text{if } \mu(i, E) \geq 0 \text{ for all } i \\ \infty, & \text{if } \mu(i, E) < 0 \text{ for any } i \end{cases}$$

Regularization Option #2 can be expressed in a number of ways. Here is one possibility:

$$R(X) = \begin{cases} 0, & \text{if } \rho(i) \leq 10 \text{ for all } i \\ (\rho(i) - 10)^2, & \text{if } 10 < \rho(i) \leq 22.5 \text{ for any } i \\ \infty, & \text{if } \rho(i) > 22.5 \text{ for any } i \end{cases}$$

where $\rho(i)$ is some estimate of density.

Regularization Option #3 can be expressed as $R(X) = \Sigma \|\nabla \rho(i)\|^2$ (easier, but gives blurry edges)

$R(X) = \Sigma \|\nabla \rho(i)\|^2$ (more difficult, but gives sharper edges)

$R(X) = \Sigma \psi(\nabla \rho(i))$ (a compromise between the two)

where $\psi$ is a robust estimator like the Huber function and $\rho$ is some estimate of density (which might be the same or different as the function used in #2).

Regularization Option #4 can be expressed by the analysis method using:

$R(X) = \|\Phi^t \rho\|$ where $\Phi^t$ is the analysis operator for an appropriate dictionary (such as wavelets).

One might also replace the norm operator with something more complicated such as a Huber function or entropy function.

Regularization Option #4 could instead be expressed by the synthesis method by, instead of representing X directly, storing a set of coefficients that can be used to synthesis X, $X = \Phi c$ where $\Phi$ is some dictionary (such as wavelets or the like) that supports tensor fields.

Then we can use the penalty $R(X) = \|c\|$ or we can replace the norm operator with any of the alternatives just mentioned.

In image processing, there are many known dictionaries $\Phi$ (whether used for analysis or synthesis), such as wavelets, curvelets, ridgelets, and the Fourier and discrete sine/cosine bases. There are also many known methods for designing dictionaries specifically tailored to particular types of images. Any such dictionaries can be used in embodiments of this invention (including building a dictionary specifically intended for cargo imaging).

Regularization Option #5 is an example of the burgeoning field of non-local image regularization, which is becoming popular for image restoration (denoising, or recovering missing pixels).

Regularization Option #6 can be expressed by $R(X) = \Sigma \|\nabla X\|^2$ $R(X) = \Sigma \|\nabla X\|$ or by summing the angles between neighbors, as in U.S. Patent Publication No. 2013/001156 A1, which is assigned to the assignee of the present invention, and is incorporated by reference herein. Any of the methods described in Holt, "Angular Regularization of Vector-Valued Signals", ICASSP 2011, which is incorporated by reference herein, for example, may also be used.

Regularization Option #9 can be implemented at least in part by designing a matrix B then using the penalty $$R(X) = \begin{cases} 0, & BX(i) \geq 0 \text{ for all } i \\ \infty, & BX(i) < 0 \text{ for any } i \end{cases}$$

where details of how to construct such a B are also described U.S. Patent Publication No. 2013/0101156 A1, which is assigned to the assignee of the present invention and is incorporated by reference herein.

Optimization Algorithm

Once we have defined the D function and zero or more R functions, we can recover X by minimizing the cost $C(X, P) = D(C,P) + \Sigma_n \lambda_n R_n$ as indicated in Step 6, above. A search algorithm known in the art may be used, or example. These include first-order gradient methods such as steepest descent, conjugate gradient search, or Nesterov's accelerated methods. It also could include second-order or quasi-second-order methods, including Newton-type methods and quasi-Newton methods (including L-BFGS). These also include proximal splitting methods, including augmented Lagrangian methods, ADMM and its variants, the Parallel-ProXimal Algorithm, the prox-lin method, iterative shrinkage, FISTA, NESTA, and the like. The choice of algorithm often depends on exactly what Regularizers are used (for example, if we switch between Regularization Option #3 vs #4 (analysis version) vs #4 (synthesis version), the fastest search algorithm might depend on which Regularization Option we choose).

There are also many prior art techniques for speeding up the search algorithm; these are generally complementary to the above techniques. These include using a direct/analytic algorithm as an initialization, multi-grid methods (i.e. coarse-to-fine progressive reconstruction), continuation methods (i.e. solve first for very large $\lambda$ and gradually decrease), as well as hardware acceleration (using clusters, GPUs, FPGAs, ASICs, or the like).

Visualization & Output

If a 3D image is reconstructed (isotropic or anisotropic) for X, any of the volume rendering methods currently in use in medical or industrial imaging (including Multi-Planar Reformatting (MPR), Maximum-Intensity-Projection (MIP), or 3D ray-tracing-based algorithms (allowing a volume to either be first sliced, or to have a fractional transparency to each voxel), may be used.

If X is reconstructed as a 2D slice or a set of 2D slices, they may be viewed in a similar manner to viewing typical 2D images, except with additional user control over the slice location(s) and orientations. As the user changes the slice locations, the reconstruction can update the image. For 3D reconstruction, this full volume may be reconstructed and then the result may be manipulated (rotate, slice, etc) without re-reconstructing.

A radiography view and a material discrimination ("MD") view may be provided. In the radiography view, a ρ image is calculated (using one of the X→ρ conversions listed above) and displayed to the user in grayscale. In the MD view, the X tensor is mapped into a more useful material space (such as atomic number) using any method from U.S. Patent Publication No. 2013/0101156 A1, which is assigned to the assignee of the present invention and is incorporated by reference herein. If there is confidence in the material assessment, the voxel may be displayed in an appropriate color, and if not, the voxel may be displayed in grayscale.

In addition to visualization, automated analysis may be performed on the images. Typically, different materials will have different X values. For example, if K=4, there is some 4-dimensional space that can be segmented into threat and non-threat regions (each of which might be made of many smaller disconnected regions). It can also be segmented directly into many smaller regions corresponding to more specific materials. In general these regions may overlap and may have soft boundaries. Voxels may be measured and classified as members of material-regions and colored appropriately (as a visualization technique) or a non-image-based response may be provided, such as an alarm bell, flashing icon, or text report, for example.

Figure 13:
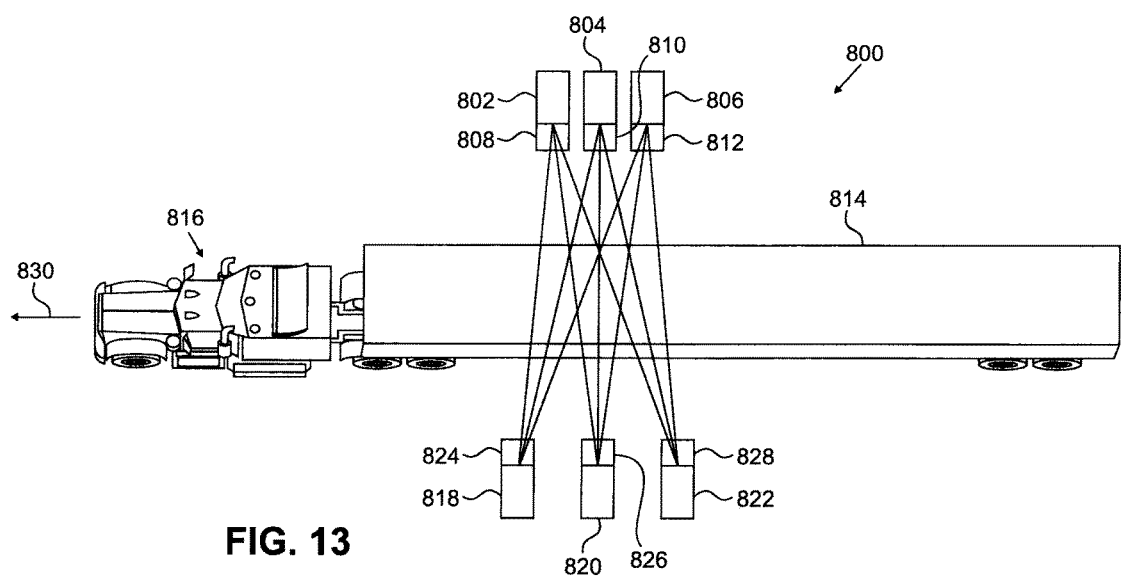
FIG. 13 is an example of a radiation scanning system, in accordance with another embodiment of the invention.

Another System for 2-D or Quasi-3D Cargo Imaging with Laminography or Dark-Field Imaging In accordance with another embodiment of the invention, a radiation scanning system 800 ("system 800") is disclosed comprising multiple sources and multiple detectors, to obtain multiple views in different planes, as shown in FIG. 13. In the system 800, three radiation sources 802, 804, 806, with collimators 808, 810, 812 respectively, are provided on one side of an object 814 to be examined. In this example, the object 814 is a cargo container supported by a truck 816. The radiation sources 802, 804, 806 each comprise a respective source of charged particles, such as an electron gun, an accelerator, and associated components, as is known in the art. An image processor 20, a display 22, a processing device 24, and memory 26 may also be provided, as discussed above with respect to FIGS. 1 and 3.

On an opposite side of the object 814 are three detector arrays 818, 820, 822, with respective collimators 824, 826, 828, respectively.

The truck 816, and object 814 may be moved through the scanning system 800 by a conveyor system 830, as discussed above. Alternatively, radiation scanning system 800 may be supported by a gantry that moves across the object 814 and truck 816, as is known in the art.

The source collimators 808, 810, 812 in this example each define three (3) radiation beams at different angles. The detector arrays 818, 820, 822 are positioned in this example to record radiation transmitted through the object 814 from each radiation source 802, 804, 806. The collimators 808, 810, 812 define three (3) respective slots that are aligned with the radiation beams to be received by each detector array 818, 820, 822. Nine distinct views of the object 814 are thereby provided.

The radiation sources 802, 804, 806 and detector arrays 818, 820, 822 are not equally spaced so that all 9 rays are at different angles. The spacings between the radiation sources 802, 804, 806 and between the detector arrays 818, 820, 822 may be chosen to provide a fairly uniformly-spaced set of angles. The numbers of radiation sources 802, 804, 806 and the detector arrays 818, 820, 822 are just an example and different numbers of sources and detectors may be provided. For example, there may be one radiation source (emitting a wide beam) and at least two detector arrays to detect the wide beam, at least two radiation sources and one detector array, at least two radiation sources and at least three detector arrays, three radiation sources and four or five detector arrays, ten radiation sources and four detector arrays, twenty radiation sources and one detector array, or one radiation source and 20 detector arrays.

One of the source collimators 808, 810, 812 may define a radiation beam that is perpendicular to the truck's axis, to provide a direct side view. The radiation sources 802, 804, 806 may be all at the same elevation, so that the difference between images from each source/detector pair is only a rotation in the horizontal plane. Some of the radiation sources 802, 804, 806 may also be at different elevations, so that some images are effectively rotated axially with respect to each other.

Figure 1:
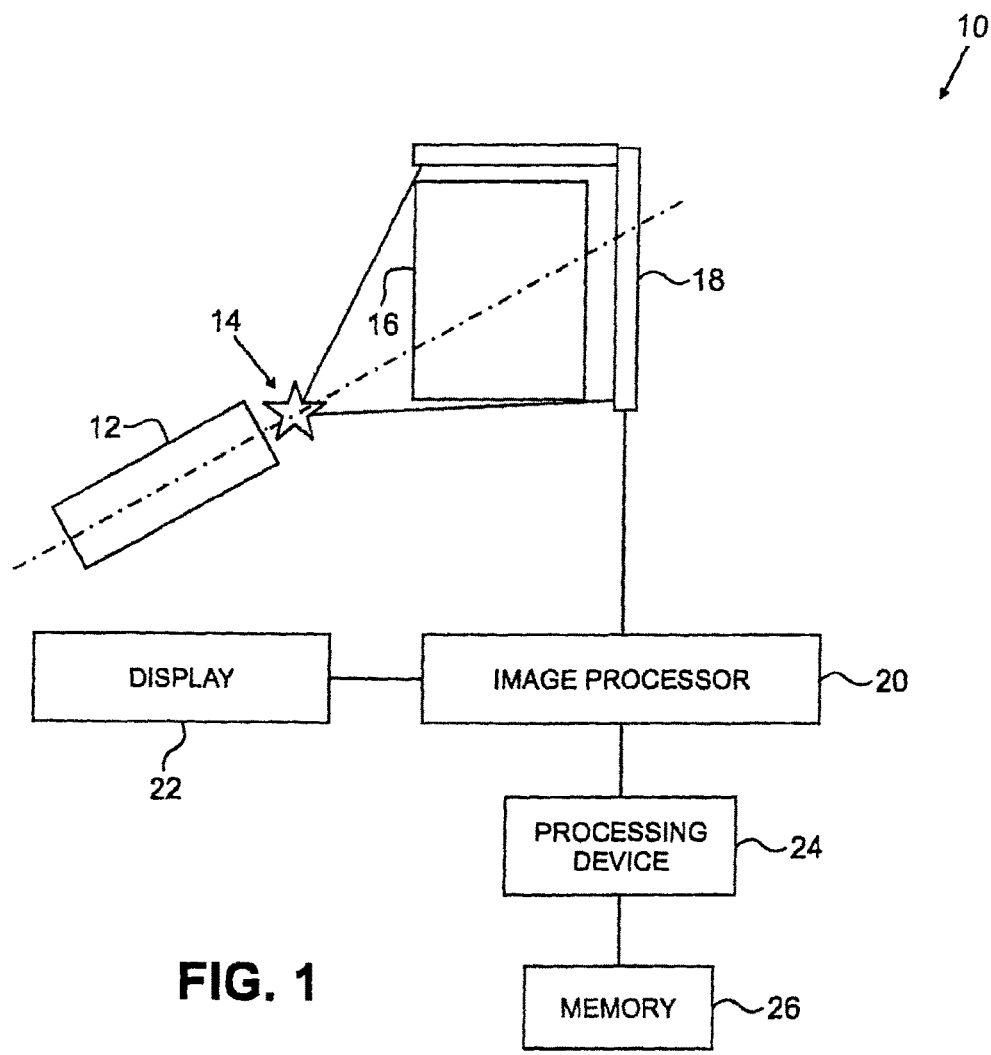
FIG. 1 is a schematic representation of an example of a typical cargo radiography system.

Operation of the radiation sources 802, 804, 806 is timed by the processing device, such as the processing device shown in FIGS. 1 and 3, for example, so that no two sources fire at the same time. This is practical to coordinate, since each source 802, 804, 806 generally has a very low duty cycle. For example, a typical Linatron®, available from Varian Medical Systems, Inc., Palo Alto, Calif., has a 3 usec pulse on a 3 msec period. In a system 800 including three radiation sources 802, 804, 806, the radiation sources may be staggered by 1 msec each.

Operation of the detectors 818, 820, 822 is coordinated with operation of the sources 802, 804, 806 by the processing device so that each time a source fires, a full measurement from each detector is collected. In the above example, each detector collects a full image every 1 msec.

Quasi-3D images may be reconstructed by the optimization algorithm, described above. 3D images may also be reconstructed from using computed laminography or tomosynthesis, or more generally, limited-view CT methods. Each view can also include multiple energies or stacked detectors, so we can incorporate material discrimination.

Figure 14:
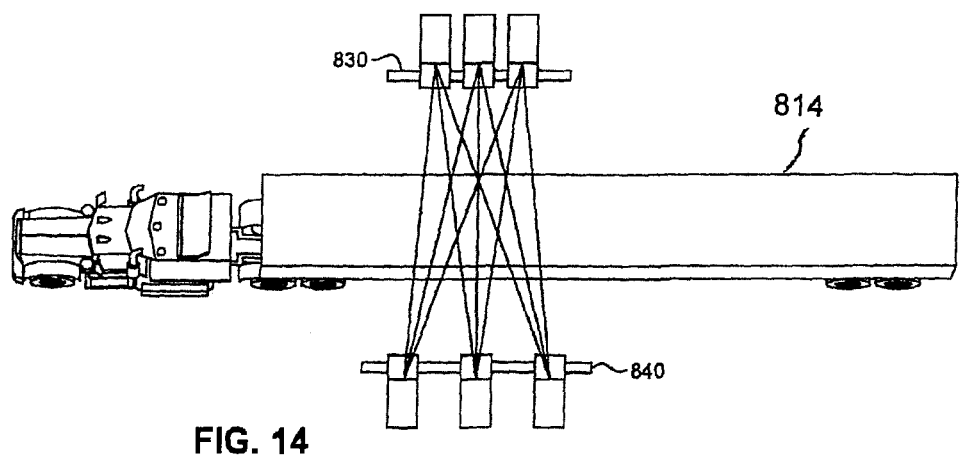
FIG. 14 shows the system of FIG. 13, with back-scatter detectors and forward-scatter detectors.

Scatter detectors may also be provided for dark-field imaging. Back-scatter detectors 830 and/or forward-scatter detectors 840 may be provided for example, as shown in FIG. 14. The back-scatter and/or forward scatter detectors 830, 840 may have configuration of the scatter detectors described above. The other components of FIG. 14 are the same as in FIG. 13.

Measurements from the scatter detectors 830, 840, particularly the scatter detector 830, are more sensitive at the faces of the object 814 so they provide additional spatial information that can be incorporated into the same 3D reconstruction. A new image may be collected from each of the scatter detectors 830, 840 for each source pulse.

Figure 2:
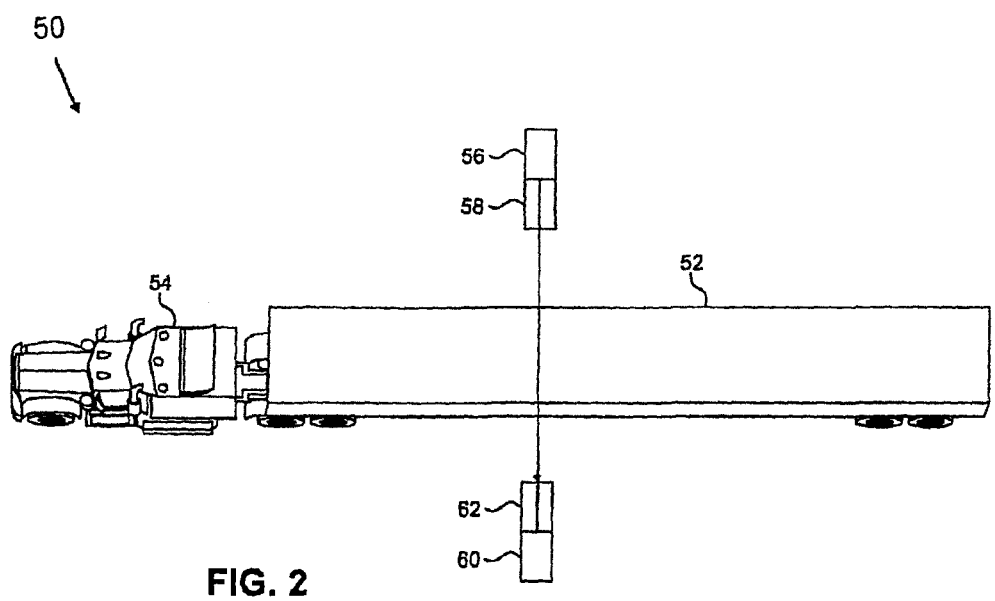
FIG. 2 is a schematic representation of another example of a radiation scanning system positioned to scan a cargo container supported by a truck.

This embodiment of the invention uses cooperative imaging components, which may scale better than dual-view systems that use two non-interfering imaging chains, with one source and one detector each. Non-interfering designs scale linearly with the number of sources and detectors. In other words, in a conventional non-interfering design, buying N times as much imaging hardware gets you N times more data. However, if there are N sources in the present embodiment of the invention, adding only one more detector gives N times more information, and if there are M detectors, then adding only one more source gives M times more information. In other words, if M and N are kept similar, buying N times as much imaging hardware can get you $N^2$ times more data, making it a far more cost effective option. In the example of FIG. 13, 9 distinct views of the object 814 are provided, but the cost of the X-ray optics are only increased by ~3×, as compared to the configuration of FIG. 2, for example.

If, for example, to make useful volumetric reconstructions, a particular imaging task takes 25× more information than currently provided by a fourth generation scanner having a source rotating around an object, within a circular detector, then to scan a cargo container or other such object 814, in the same amount of time, a volumetric scanner using independent chains would be ~25× more expensive than the current fourth generation scanner, which could be prohibitive. However, in embodiments of the present invention, the scanner would be ~5× more expensive than the current fourth generation scanner, which is much more likely to become practically useful. Additional costs may be saved by sharing a power source, such as a modulator, and/or other components among the radiation sources 802, 804, 806.

Although example embodiments have been shown and described in this Specification and Figures, it would be appreciated by those skilled in the art that changes may be made to the illustrated and/or described example embodiments without departing from the scope of the invention, which is defined by the following claims.

We claim:

1. A radiation scanning system to examine an object, the system comprising:
   a source of charged particles;
   a radio frequency accelerator to accelerate charged particles provided by the source of charged particles, the radio frequency accelerator having an input to receive the charged particles and an output for exit of accelerated charged particles from the radio frequency accelerator;
   a first electromagnet;
   a first pipe at the output of the radio frequency accelerator to guide accelerated charged particles along a path to the first electromagnet;
   a second pipe coupled to the first electromagnet, and a third pipe coupled to the first electromagnet, wherein the first electromagnet is configured to selectively allow passage of the accelerated charged particles to the third pipe and to selectively direct accelerated charged particles to the second pipe;
   at least one second electromagnet along the third pipe;
   a fourth pipe coupled to the at least one second electromagnet, wherein the at least one second electromagnet is configured to deflect accelerated charged particles to the fourth pipe;
   at least one first target, at least one second target, and at least one third target proximate each of the second pipe, the third pipe, and the fourth pipe, respectively, wherein impact of the at least one first target, the at least one second target, and the at least one third target by the accelerated charged particles causes generation of radiation to scan the object at different viewing angles;
   a respective third electromagnet coupled to the second pipe, the third pipe, and/or the fourth pipe, respectively, to selectively direct the accelerated charged particles to one of the at least one first target, the at least one second target, and/or the at least one third target, respectively;
   at least one detector to detect radiation generated by the at least one first target, the at least one second target, and the at least one third target, after interacting with the object; and
   at least one processing device to control operation of the first electromagnet, the at least one second electromagnet, and the third electromagnet, and reconstruct images from data collected from the at least one detector.

2. The radiation scanning system of claim 1, further comprising:
   a conveyor system to move the object through the generated radiation.

3. The radiation scanning system of claim 1, wherein:
   at least some of the at least one first target, the at least one second target, and the at least one third target lie in different planes; and
   the at least one detector comprises at least one respective detector array facing one or more of the at least one first target, the at least one second target, and the at least one third target, on an opposite side of the object as the respective target.

4. The radiation scanning system of claim 3, further comprising at least one scatter detector adjacent to one or more of the at least one respective detector array to detect radiation scattered by the object.

5. The radiation scanning system of claim 3, wherein the at least one respective detector array comprises an L-shaped detector array and/or a U-shaped detector array.

6. The radiation scanning system of claim 3, wherein the at least one respective detector array comprises a respective module comprising detector elements and vanes, the vanes facing one of the at least one first target, or one of the at least one second target, or one of the at least one third target to allow radiation transmitted through the object, from the one of the at least one first target, or the one of the at least one second target, or the one of the at least one third target, to be recorded by the detector elements and to reject scattered radiation from being recorded by the detector elements.

7. The radiation scanning system of claim 1, further comprising at least one fourth target and at least one fifth target proximate the second pipe, the third pipe, and/or the fourth pipe.

8. The radiation scanning system of claim 7, further comprising at least one sixth target and at least one seventh target proximate the second pipe, the third pipe, and/or the fourth pipe.

9. The radiation scanning system of claim 1, wherein:
   the second pipe, the third pipe, and the fourth pipe and the at least one first target, the at least one second target, and the at least one third target adjacent the second pipe, the third pipe, and the fourth pipe, respectively, lie in the same plane; and
   the at least one detector comprises a wrap around detector array defining a region containing the object, wherein the at least one first target, the at least one second target, and the at least one third target are within the region, the wrap around detector array comprising respective detector segments spaced to allow passage of accelerated charged particles to the at least one first target, the at least one second target, and the at least one third target.

10. The radiation scanning system of claim 9, wherein the wrap around detector array comprises at least one module comprising detector elements and parallel vanes, the at least one module being rotatable so that the parallel vanes face one of the at least one first target, or one of the at least one second target, or one of the at least third target that is emitting radiation during operation, to allow radiation transmitted through the object, from the respective one of the at least one first target, or one of the at least one second target, or one of the at least third target, to be recorded by the detector elements of the at least one module and to reject scattered radiation from being recorded by the detector elements.

11. The radiation scanning system of claim 1, wherein the at least one processing device is further configured to reconstruct quasi-three-dimensional images from data recorded by the at least one detector.

12. A radiation scanning system to examine an object comprising:
a plurality of stationary radiation sources facing a first side of the object, each radiation source being configured to emit a respective radiation beam from a respective output;
a plurality of collimators;
wherein a respective collimator of the plurality of collimators is proximate the respective output of at least some of the plurality of stationary radiation sources, each respective collimator being configured to collimate the respective radiation beam from a respective stationary radiation source into a first respective plurality of radiation beams angled with respect to each other, to scan an object at a second plurality of angles;
a plurality of detectors positioned on a second side of the object opposite the first side to detect each of the first respective plurality of radiation beams at the different angles; and
a processing device to reconstruct images from data collected from the at least some of the plurality of detectors.

13. The radiation scanning system of claim 12, further comprising:
a plurality of second collimators, wherein a respective one of the plurality of second collimators is configured to collimate some of the plurality of radiation beams after interaction with the object, prior to detection by a respective detector of the plurality of detectors.

14. The radiation scanning system of claim 12, wherein:
the plurality of stationary radiation sources comprise three radiation sources;
the plurality of radiation detectors comprise three radiation detectors; and
the plurality of collimators comprise three collimators;
wherein each of the three collimators collimates the radiation beam from a respective one of the three radiation sources into three radiation beams angled with respect to each other, and
each of the three radiation beams from each of the three radiation sources is detected by each of the three radiation detectors.

15. The radiation scanning system of claim 12, further comprising at least one scatter detector adjacent to at least one of the plurality of detectors.

16. The radiation scanning system of claim 12, further comprising at least one scatter detector adjacent to at least one of the plurality of stationary radiation sources to detect scattered radiation.

17. The radiation scanning system of claim 12, wherein the processing device is configured to reconstruct quasi-three-dimensional images.

18. A method of reconstructing images, comprising:
scanning an object by a plurality of radiation beams generated by a plurality of radiation sources at a plurality of angles;
detecting the plurality of radiation beams after interacting with the object to obtain measured data;
reconstructing images of the object from projection measurements in a plurality of different planes, by:
making an initial estimate of an image of the object;
forming a current estimate of the image of the object by iteratively updating the initial estimate to improve the likelihood of the current estimate, based, at least in part, on a feasibility model defining a likelihood that the current estimate occurs in nature and an imaging model defining a likelihood that the measured data would have been collected based, at least in part, on the current estimate.

19. The method of claim 18, wherein the initial estimate of the image comprises material information.

20. The method of claim 18, comprising iteratively updating the initial estimate until the iteratively updating has converged to an underlying image that is most likely.

* * * * *